(12) United States Patent
Jiang et al.

(10) Patent No.: US 7,338,772 B2
(45) Date of Patent: Mar. 4, 2008

(54) G-PROTEIN COUPLED RECEPTOR LIGANDS AND METHODS

(75) Inventors: Ying Jiang, Scotch Plains, NJ (US); Fang Liang Zhang, Fanwood, NJ (US); Nicholas J. Murgolo, Millington, NJ (US); Lin Luo, Edison, NJ (US); Jason S. Simon, Westfield, NJ (US)

(73) Assignee: Schering Corporation, Kenilworth, NJ (US)

( * ) Notice: Subject to any disclaimer, the term of this patent is extended or adjusted under 35 U.S.C. 154(b) by 560 days.

(21) Appl. No.: 10/411,545

(22) Filed: Apr. 10, 2003

(65) Prior Publication Data

US 2003/0223992 A1    Dec. 4, 2003

Related U.S. Application Data

(60) Provisional application No. 60/372,640, filed on Apr. 12, 2002.

(51) Int. Cl.
*G01N 33/566* (2006.01)
(52) U.S. Cl. ..................... 435/7.21; 435/7.2; 436/501
(58) Field of Classification Search ..................... None
See application file for complete search history.

(56) References Cited

U.S. PATENT DOCUMENTS

| 6,927,041 B2 * | 8/2005 | Zhelnin et al. ............ 435/69.1 |
| 2003/0223992 A1 | 12/2003 | Jiang et al. |
| 2004/0248790 A1 * | 12/2004 | Hinuma et al. |

FOREIGN PATENT DOCUMENTS

| EP | 1 207 201 A1 * | 5/2002 |
| WO | WO97/37967 | 10/1997 |
| WO | WO99/32519 | 7/1999 |
| WO | WO 00/11015 | 3/2000 |
| WO | WO 00/22131 | 4/2000 |
| WO | WO 00/31258 | 6/2000 |
| WO | WO00/66151 | 11/2000 |
| WO | WO 00/78809 A1 | 12/2000 |
| WO | WO 01/16316 * | 3/2001 |
| WO | WO 01/16316 A1 | 3/2001 |
| WO | WO 01/48189 A1 | 7/2001 |

OTHER PUBLICATIONS

Jiang-Y et al. J. Biol. Chem. 278(30)27652-27657)2003.*
Nagai-G et al., Biochem. Biophys. Res. Com. 248(733-737)1998.*
Fukusumi-S. et al., J. Biol. Chem. 278(46387-46395)2003.*
Bowie et al., 1990, Science 247:1306-1310.*
Guo-HH et al. PNAS 101(25)9205-9210, 2004.*
PCT/US03/11159 Patent Corporation Treaty International Search Report (5 pgs.).
Ensembl genome database entry, SP9155, 2006.
Takayasu et al., A neuropeptide ligand of the G protein-coupled receptor GPR103 regulates feeding, behavioral arousal, and blood pressure in mice. Proc Natl Acad Sci U S A. May 9, 2006;103(19):7438-43.
Chartrel et al., Identification of 26RFa, a hypothalamic neuropeptide of the RFamide peptide family with orexigenic activity. Proc. Natl. Acad. Sci. U S A. Dec. 9, 2003;100(25):15247-52.
Chartrel et al., Identification of 26RFa from frog brain: a novel hypothalamic neuropeptide with orexigenic activity in mammals. Ann. N.Y. Acad Sci. Apr. 2005;1040:80-3.
Do Rego et al., Behavioral effects of 26RFamide and related peptides. Peptides (2006) in press.
Moriya et al., RFamide peptide QRFP43 causes obesity with hyperphagia and reduced thermogenesis in mice. Endocrinology. Jun. 2006;147(6):2916-22.
Lee et al., Discovery and mapping of ten novel G protein-coupled receptor genes. Gene (2001) 275: 83-91.
Sequence Disclosure-Genbank Accession No. BB200502, Jun. 30, 2000.
Sequence Disclosure-Genbank Accession No. BB634210, Aug. 31, 2001.
Sequence Disclosure-Genbank Accession No. BB613620, Aug. 31, 2001.
Sequence Disclosure-Genbank Accession No. XM_071001, Aug. 1, 2002.
Sequence Disclosure-Genbank Accession No. AL161733, Dec. 3, 2001.
Sequence Disclosure-Genbank Accession No. BF167714, Oct. 27, 2000.
Liu et al., J. Biol. Chem. (2001) 276(40):36961-36969.
Li et al., Brain Research (1999) 848:26-34.
Ying Jiang et al, Identification and Characterization of a Novel RF-amide Peptide for Orphan G-Protein-Coupled Receptor SP9155, Journal of Bio Chem, vol. 278, No. 30, pp. 27652-27657, 2003.
Ying Jiang et al, Identification and Characterization of a Novel Peptide for Orphan G-Protein Coupled Receptor SP9155, Biopolymers, vol. 71, No. 3, pp. 296, 2003.
Lee, Dennis K., et al., Discovery and mapping of ten novel G protein-coupled receptor genes. Gene (2001) 275:83-91.
Jiang, Ying, et al., PepPat, a pattern-based oligopeptide homology search method and the identification of a novel tachykinin-like peptide Mammalian Genome (2003) 14:341-349.
Klein, Robert F., et al., Confirmation and Fine Mapping of Chromosomal Regions Influencing Peak Bone Mass in Mice. J. Bone Min. Res. (2001) 16(11):1953-1961.
Benes, Helen et al., Chromosomal Mapping of Osteopenia-Associated Quantitative Trait Loci Using Closely Related Mouse Strains. J. Bone Min. Res (2000) 15(4):626-633
Joost, Patrick, et al., Phylogenetic analysis of 277 human G-protein-coupled receptors as a tool for the prediction of orphan receptor ligands. Genome Biology 2002, 3(11):research0063.1-0063.16.

* cited by examiner

*Primary Examiner*—John Ulm

(57) ABSTRACT

The present invention relates to RF-amide peptides and their use for treating, preventing and curing neurological and metabolic medical disorders. The invention also relates to methods for modulating a G-protein coupled receptor and for identifying substances which modulate the receptor.

27 Claims, No Drawings

SEQUENCE LISTING

```
<160> NUMBER OF SEQ ID NOS: 20

<210> SEQ ID NO 1
<211> LENGTH: 1296
<212> TYPE: DNA
<213> ORGANISM: Homo sapiens
<220> FEATURE:
<221> NAME/KEY: CDS
<222> LOCATION: 1..1296
<223> OTHER INFORMATION:
<220> FEATURE:
<221> NAME/KEY: VARIANT
<222> LOCATION: 154
<223> OTHER INFORMATION: r
<220> FEATURE:
<221> NAME/KEY: VARIANT
<222> LOCATION: 181
<223> OTHER INFORMATION: k
<220> FEATURE:
<221> NAME/KEY: VARIANT
<222> LOCATION: 206
<223> OTHER INFORMATION: k
<220> FEATURE:
<221> NAME/KEY: VARIANT
<222> LOCATION: 208
<223> OTHER INFORMATION: k
<220> FEATURE:
<221> NAME/KEY: VARIANT
<222> LOCATION: 447
<223> OTHER INFORMATION: k
<220> FEATURE:
<221> NAME/KEY: VARIANT
<222> LOCATION: 748
<223> OTHER INFORMATION: k
<220> FEATURE:
<221> NAME/KEY: VARIANT
<222> LOCATION: 1031
<223> OTHER INFORMATION: y
<220> FEATURE:
<221> NAME/KEY: VARIANT
<222> LOCATION: 1111
<223> OTHER INFORMATION: y
<220> FEATURE:
<221> NAME/KEY: VARIANT
<222> LOCATION: 1162
<223> OTHER INFORMATION: r
<220> FEATURE:
<221> NAME/KEY: VARIANT
<222> LOCATION: 1228
<223> OTHER INFORMATION: y

<400> SEQUENCE: 1 atg cag gcg ctt aac att acc ccg gag cag ttc tct cgg ctg ctg cgg      48
Met Gln Ala Leu Asn Ile Thr Pro Glu Gln Phe Ser Arg Leu Leu Arg
1               5                   10                  15 gac cac aac ctg acg cgg gag cag ttc atc gct ctg tac cgg ctg cga      96
Asp His Asn Leu Thr Arg Glu Gln Phe Ile Ala Leu Tyr Arg Leu Arg
            20                  25                  30 ccg ctc gtc tac acc cca gag ctg ccg gga cgc gcc aag ctg gcc ctc     144
Pro Leu Val Tyr Thr Pro Glu Leu Pro Gly Arg Ala Lys Leu Ala Leu
        35                  40                  45
```

-continued

| | |
|---|---|
| gtg ctc acc ggc gtg ctc atc ttc gcc ctg gcg ctc ttt ggc aat gct<br>Val Leu Thr Gly Val Leu Ile Phe Ala Leu Ala Leu Phe Gly Asn Ala<br>50                           55                     60 | 192 |
| ctg gtg ttc tac gtg gtg acc cgc agc aag gcc atg cgc acc gtc acc<br>Leu Val Phe Tyr Val Val Thr Arg Ser Lys Ala Met Arg Thr Val Thr<br>65                           70                     75                     80 | 240 |
| aac atc ttt atc tgc tcc ttg gcg ctc agt gac ctg ctc atc acc ttc<br>Asn Ile Phe Ile Cys Ser Leu Ala Leu Ser Asp Leu Leu Ile Thr Phe<br>               85                     90                     95 | 288 |
| ttc tgc att ccc gtc acc atg ctc cag aac att tcc gac aac tgg ctg<br>Phe Cys Ile Pro Val Thr Met Leu Gln Asn Ile Ser Asp Asn Trp Leu<br>              100                  105               110 | 336 |
| ggg ggt gct ttc att tgc aag atg gtg cca ttt gtc cag tct acc gct<br>Gly Gly Ala Phe Ile Cys Lys Met Val Pro Phe Val Gln Ser Thr Ala<br>              115                  120               125 | 384 |
| gtt gtg aca gaa atc ctc act atg acc tgc att gct gtg gaa agg cac<br>Val Val Thr Glu Ile Leu Thr Met Thr Cys Ile Ala Val Glu Arg His<br>130                          135                  140 | 432 |
| cag gga ctt gtg cat cct ttt aaa atg aag tgg caa tac acc aac cga<br>Gln Gly Leu Val His Pro Phe Lys Met Lys Trp Gln Tyr Thr Asn Arg<br>145                       150                  155               160 | 480 |
| agg gct ttc aca atg cta ggt gtg gtc tgg ctg gtg gca gtc atc gta<br>Arg Ala Phe Thr Met Leu Gly Val Val Trp Leu Val Ala Val Ile Val<br>                    165                  170               175 | 528 |
| gga tca ccc atg tgg cac gtg caa caa ctt gag atc aaa tat gac ttc<br>Gly Ser Pro Met Trp His Val Gln Gln Leu Glu Ile Lys Tyr Asp Phe<br>                    180                  185               190 | 576 |
| cta tat gaa aag gaa cac atc tgc tgc tta gaa gag tgg acc agc cct<br>Leu Tyr Glu Lys Glu His Ile Cys Cys Leu Glu Glu Trp Thr Ser Pro<br>                   195                  200               205 | 624 |
| gtg cac cag aag atc tac acc acc ttc atc ctt gtc atc ctc ttc ctc<br>Val His Gln Lys Ile Tyr Thr Thr Phe Ile Leu Val Ile Leu Phe Leu<br>210                          215                  220 | 672 |
| ctg cct ctt atg gtg atg ctt att ctg tac agt aaa att ggt tat gaa<br>Leu Pro Leu Met Val Met Leu Ile Leu Tyr Ser Lys Ile Gly Tyr Glu<br>225                          230                  235               240 | 720 |
| ctt tgg ata aag aaa aga gtt ggg gat ggt tca gtg ctt cga act att<br>Leu Trp Ile Lys Lys Arg Val Gly Asp Gly Ser Val Leu Arg Thr Ile<br>                    245                  250               255 | 768 |
| cat gga aaa gaa atg tcc aaa ata gcc agg aag aag aaa cga gct gtc<br>His Gly Lys Glu Met Ser Lys Ile Ala Arg Lys Lys Lys Arg Ala Val<br>                   260                  265               270 | 816 |
| att atg atg gtg aca gtg gtg gct ctc ttt gct gtg tgc tgg gca cca<br>Ile Met Met Val Thr Val Val Ala Leu Phe Ala Val Cys Trp Ala Pro<br>               275                  280               285 | 864 |
| ttc cat gtt gtc cat atg atg att gaa tac agt aat ttt gaa aag gaa<br>Phe His Val Val His Met Met Ile Glu Tyr Ser Asn Phe Glu Lys Glu<br>290                          295                  300 | 912 |
| tat gat gat gtc aca atc aag atg att ttt gct atc gtg caa att att<br>Tyr Asp Asp Val Thr Ile Lys Met Ile Phe Ala Ile Val Gln Ile Ile<br>305                          310                  315               320 | 960 |
| gga ttt tcc aac tcc atc tgt aat ccc att gtc tat gca ttt atg aat<br>Gly Phe Ser Asn Ser Ile Cys Asn Pro Ile Val Tyr Ala Phe Met Asn<br>                    325                  330               335 | 1008 |
| gaa aac ttc aaa aaa aat gtt ttg tct gca gtt tgt tat tgc ata gta<br>Glu Asn Phe Lys Lys Asn Val Leu Ser Ala Val Cys Tyr Cys Ile Val<br>                    340                  345               350 | 1056 |
| aat aaa acc ttc tct cca gca caa agg cat gga aat tca gga att aca<br>Asn Lys Thr Phe Ser Pro Ala Gln Arg His Gly Asn Ser Gly Ile Thr<br>                   355                  360               365 | 1104 |

-continued

```
atg atg cgg aag aaa gca aag ttt tcc ctc aga gag aat cca gtg gag    1152
Met Met Arg Lys Lys Ala Lys Phe Ser Leu Arg Glu Asn Pro Val Glu
    370             375                 380 gaa acc aaa gga gaa gca ttc agt gat ggc aac att gaa gtc aaa ttg    1200
Glu Thr Lys Gly Glu Ala Phe Ser Asp Gly Asn Ile Glu Val Lys Leu
385                 390                 395                 400 tgt gaa cag aca gag gag aag aaa aag ctc aaa cga cat ctt gct ctc    1248
Cys Glu Gln Thr Glu Glu Lys Lys Lys Leu Lys Arg His Leu Ala Leu
                405                 410                 415 ttt agg tct gaa ctg gct gag aat tct cct tta gac agt ggg cat taa    1296
Phe Arg Ser Glu Leu Ala Glu Asn Ser Pro Leu Asp Ser Gly His
                420                 425                 430
```

<210> SEQ ID NO 2
<211> LENGTH: 431
<212> TYPE: PRT
<213> ORGANISM: Homo sapiens
<220> FEATURE:
<221> NAME/KEY: MISC_FEATURE
<222> LOCATION: 52
<223> OTHER INFORMATION: Ser or Gly
<220> FEATURE:
<221> NAME/KEY: MISC_FEATURE
<222> LOCATION: 410
<223> OTHER INFORMATION: Phe or Leu
<220> FEATURE:
<221> NAME/KEY: MISC_FEATURE
<222> LOCATION: 388
<223> OTHER INFORMATION: Arg or Gly
<220> FEATURE:
<221> NAME/KEY: MISC_FEATURE
<222> LOCATION: 371
<223> OTHER INFORMATION: Trp or Arg
<220> FEATURE:
<221> NAME/KEY: MISC_FEATURE
<222> LOCATION: 344
<223> OTHER INFORMATION: Ser or Leu
<220> FEATURE:
<221> NAME/KEY: MISC_FEATURE
<222> LOCATION: 250
<223> OTHER INFORMATION: Cys or Gly
<220> FEATURE:
<221> NAME/KEY: MISC_FEATURE
<222> LOCATION: 149
<223> OTHER INFORMATION: Gln or Lys
<220> FEATURE:
<221> NAME/KEY: MISC_FEATURE
<222> LOCATION: 70
<223> OTHER INFORMATION: Leu or Val
<220> FEATURE:
<221> NAME/KEY: MISC_FEATURE
<222> LOCATION: 69
<223> OTHER INFORMATION: Gly or Val
<220> FEATURE:
<221> NAME/KEY: MISC_FEATURE
<222> LOCATION: 61
<223> OTHER INFORMATION: Val or Phe

<400> SEQUENCE: 2

```
Met Gln Ala Leu Asn Ile Thr Pro Glu Gln Phe Ser Arg Leu Leu Arg
1               5                   10                  15

Asp His Asn Leu Thr Arg Glu Gln Phe Ile Ala Leu Tyr Arg Leu Arg
                20                  25                  30

Pro Leu Val Tyr Thr Pro Glu Leu Pro Gly Arg Ala Lys Leu Ala Leu
            35                  40                  45

Val Leu Thr Xaa Val Leu Ile Phe Ala Leu Ala Leu Xaa Gly Asn Ala
        50                  55                  60

Leu Val Phe Tyr Xaa Xaa Thr Arg Ser Lys Ala Met Arg Thr Val Thr
65                  70                  75                  80
```

```
Asn Ile Phe Ile Cys Ser Leu Ala Leu Ser Asp Leu Leu Ile Thr Phe
                 85                  90                  95

Phe Cys Ile Pro Val Thr Met Leu Gln Asn Ile Ser Asp Asn Trp Leu
            100                 105                 110

Gly Gly Ala Phe Ile Cys Lys Met Val Pro Phe Val Gln Ser Thr Ala
            115                 120                 125

Val Val Thr Glu Ile Leu Thr Met Thr Cys Ile Ala Val Glu Arg His
        130                 135                 140

Gln Gly Leu Val Xaa Pro Phe Lys Met Lys Trp Gln Tyr Thr Asn Arg
145                 150                 155                 160

Arg Ala Phe Thr Met Leu Gly Val Val Trp Leu Val Ala Val Ile Val
                165                 170                 175

Gly Ser Pro Met Trp His Val Gln Gln Leu Glu Ile Lys Tyr Asp Phe
            180                 185                 190

Leu Tyr Glu Lys Glu His Ile Cys Cys Leu Glu Trp Thr Ser Pro
        195                 200                 205

Val His Gln Lys Ile Tyr Thr Thr Phe Ile Leu Val Ile Leu Phe Leu
    210                 215                 220

Leu Pro Leu Met Val Met Leu Ile Leu Tyr Ser Lys Ile Gly Tyr Glu
225                 230                 235                 240

Leu Trp Ile Lys Lys Arg Val Gly Asp Xaa Ser Val Leu Arg Thr Ile
                245                 250                 255

His Gly Lys Glu Met Ser Lys Ile Ala Arg Lys Lys Arg Ala Val
            260                 265                 270

Ile Met Met Val Thr Val Val Ala Leu Phe Ala Val Cys Trp Ala Pro
        275                 280                 285

Phe His Val Val His Met Met Ile Glu Tyr Ser Asn Phe Glu Lys Glu
    290                 295                 300

Tyr Asp Asp Val Thr Ile Lys Met Ile Phe Ala Ile Val Gln Ile Ile
305                 310                 315                 320

Gly Phe Ser Asn Ser Ile Cys Asn Pro Ile Val Tyr Ala Phe Met Asn
                325                 330                 335

Glu Asn Phe Lys Lys Asn Val Xaa Ser Ala Val Cys Tyr Cys Ile Val
            340                 345                 350

Asn Lys Thr Phe Ser Pro Ala Gln Arg His Gly Asn Ser Gly Ile Thr
        355                 360                 365

Met Met Xaa Lys Lys Ala Lys Phe Ser Leu Arg Glu Asn Pro Val Glu
    370                 375                 380

Glu Thr Lys Xaa Glu Ala Phe Ser Asp Gly Asn Ile Glu Val Lys Leu
385                 390                 395                 400

Cys Glu Gln Thr Glu Glu Lys Lys Lys Xaa Lys Arg His Leu Ala Leu
                405                 410                 415

Phe Arg Ser Glu Leu Ala Glu Asn Ser Pro Leu Asp Ser Gly His
            420                 425                 430

<210> SEQ ID NO 3
<211> LENGTH: 411
<212> TYPE: DNA
<213> ORGANISM: Homo sapiens
<220> FEATURE:
<221> NAME/KEY: CDS
<222> LOCATION: 1..411
<223> OTHER INFORMATION:
<220> FEATURE:
<221> NAME/KEY: VARIANT
<222> LOCATION: 76
```

<223> OTHER INFORMATION: s
<220> FEATURE:
<221> NAME/KEY: VARIANT
<222> LOCATION: 103
<223> OTHER INFORMATION: r
<220> FEATURE:
<221> NAME/KEY: VARIANT
<222> LOCATION: 139
<223> OTHER INFORMATION: y
<220> FEATURE:
<221> NAME/KEY: VARIANT
<222> LOCATION: 203
<223> OTHER INFORMATION: w
<220> FEATURE:
<221> NAME/KEY: VARIANT
<222> LOCATION: 239
<223> OTHER INFORMATION: r

<400> SEQUENCE: 3

| | | | | | | | | | | | | | | | | |
|---|---|---|---|---|---|---|---|---|---|---|---|---|---|---|---|---|
| atg | gta | agg | cct | tac | ccc | ctg | atc | tac | ttc | ctc | ttc | ctg | ccg | ctg | ggc | 48 |
| Met | Val | Arg | Pro | Tyr | Pro | Leu | Ile | Tyr | Phe | Leu | Phe | Leu | Pro | Leu | Gly | |
| 1 | | | | 5 | | | | | 10 | | | | | 15 | | |
| gcc | tgc | ttc | cct | cta | ctg | gac | aga | aga | gag | ccc | aca | gac | gcc | atg | ggt | 96 |
| Ala | Cys | Phe | Pro | Leu | Leu | Asp | Arg | Arg | Glu | Pro | Thr | Asp | Ala | Met | Gly | |
| | | | | 20 | | | | | 25 | | | | | 30 | | |
| ggc | ctc | gga | gct | gga | gaa | cgc | tgg | gcc | gac | ctg | gcc | atg | ggg | ccc | cga | 144 |
| Gly | Leu | Gly | Ala | Gly | Glu | Arg | Trp | Ala | Asp | Leu | Ala | Met | Gly | Pro | Arg | |
| | | 35 | | | | | 40 | | | | | 45 | | | | |
| ccc | cac | tcc | gtg | tgg | ggt | tcc | tct | cgg | tgg | ctg | aga | gct | tca | cag | cca | 192 |
| Pro | His | Ser | Val | Trp | Gly | Ser | Ser | Arg | Trp | Leu | Arg | Ala | Ser | Gln | Pro | |
| | 50 | | | | | 55 | | | | | 60 | | | | | |
| cag | gcc | ctg | ctt | gtc | ata | gcc | agg | ggg | ctg | cag | aca | tcg | ggc | aga | gag | 240 |
| Gln | Ala | Leu | Leu | Val | Ile | Ala | Arg | Gly | Leu | Gln | Thr | Ser | Gly | Arg | Glu | |
| 65 | | | | | 70 | | | | | 75 | | | | | 80 | |
| cat | gct | ggc | tgc | aga | ttc | cgc | ttc | ggg | agg | cag | gac | gaa | ggc | agt | gag | 288 |
| His | Ala | Gly | Cys | Arg | Phe | Arg | Phe | Gly | Arg | Gln | Asp | Glu | Gly | Ser | Glu | |
| | | | | 85 | | | | | 90 | | | | | 95 | | |
| gcc | acc | ggc | ttc | ctc | cct | gct | gcg | ggg | gag | aag | acc | agc | ggc | ccg | tta | 336 |
| Ala | Thr | Gly | Phe | Leu | Pro | Ala | Ala | Gly | Glu | Lys | Thr | Ser | Gly | Pro | Leu | |
| | | | | 100 | | | | | 105 | | | | | 110 | | |
| ggg | aac | ctg | gct | gag | gag | ctc | aat | ggc | tac | agc | agg | aag | aaa | ggc | ggc | 384 |
| Gly | Asn | Leu | Ala | Glu | Glu | Leu | Asn | Gly | Tyr | Ser | Arg | Lys | Lys | Gly | Gly | |
| | | | 115 | | | | | 120 | | | | | 125 | | | |
| ttc | agc | ttc | cgc | ttc | ggt | cgg | cgg | tga | | | | | | | | 411 |
| Phe | Ser | Phe | Arg | Phe | Gly | Arg | Arg | | | | | | | | | |
| | 130 | | | | | 135 | | | | | | | | | | |

<210> SEQ ID NO 4
<211> LENGTH: 136
<212> TYPE: PRT
<213> ORGANISM: Homo sapiens
<220> FEATURE:
<221> NAME/KEY: MISC_FEATURE
<222> LOCATION: 47
<223> OTHER INFORMATION: Ser or Pro
<220> FEATURE:
<221> NAME/KEY: MISC_FEATURE
<222> LOCATION: 80
<223> OTHER INFORMATION: Gly or Glu
<220> FEATURE:
<221> NAME/KEY: MISC_FEATURE
<222> LOCATION: 68
<223> OTHER INFORMATION: His or Leu
<220> FEATURE:
<221> NAME/KEY: MISC_FEATURE
<222> LOCATION: 35
<223> OTHER INFORMATION: Arg or Gly
<220> FEATURE:
<221> NAME/KEY: MISC_FEATURE

```
<222> LOCATION: 26
<223> OTHER INFORMATION: Gln or Glu

<400> SEQUENCE: 4

Met Val Arg Pro Tyr Pro Leu Ile Tyr Phe Leu Phe Leu Pro Leu Gly
1               5                   10                  15

Ala Cys Phe Pro Leu Leu Asp Arg Arg Xaa Pro Thr Asp Ala Met Gly
            20                  25                  30

Gly Leu Xaa Ala Gly Glu Arg Trp Ala Asp Leu Ala Met Gly Xaa Arg
        35                  40                  45

Pro His Ser Val Trp Gly Ser Ser Arg Trp Leu Arg Ala Ser Gln Pro
    50                  55                  60

Gln Ala Leu Xaa Val Ile Ala Arg Gly Leu Gln Thr Ser Gly Arg Xaa
65                  70                  75                  80

His Ala Gly Cys Arg Phe Arg Phe Gly Arg Gln Asp Glu Gly Ser Glu
                85                  90                  95

Ala Thr Gly Phe Leu Pro Ala Ala Gly Glu Lys Thr Ser Gly Pro Leu
            100                 105                 110

Gly Asn Leu Ala Glu Glu Leu Asn Gly Tyr Ser Arg Lys Lys Gly Gly
        115                 120                 125

Phe Ser Phe Arg Phe Gly Arg Arg
    130                 135

<210> SEQ ID NO 5
<211> LENGTH: 9
<212> TYPE: PRT
<213> ORGANISM: Homo sapiens

<400> SEQUENCE: 5

Glu His Ala Gly Cys Arg Phe Arg Phe
1               5

<210> SEQ ID NO 6
<211> LENGTH: 16
<212> TYPE: PRT
<213> ORGANISM: Homo sapiens

<400> SEQUENCE: 6

Gly Leu Gln Thr Ser Gly Arg Glu His Ala Gly Cys Arg Phe Arg Phe
1               5                   10                  15

<210> SEQ ID NO 7
<211> LENGTH: 28
<212> TYPE: PRT
<213> ORGANISM: Homo sapiens

<400> SEQUENCE: 7

Ala Ser Gln Pro Gln Ala Leu Leu Val Ile Ala Arg Gly Leu Gln Thr
1               5                   10                  15

Ser Gly Arg Glu His Ala Gly Cys Arg Phe Arg Phe
            20                  25

<210> SEQ ID NO 8
<211> LENGTH: 7
<212> TYPE: PRT
<213> ORGANISM: Homo sapiens

<400> SEQUENCE: 8

Gly Gly Phe Ser Phe Arg Phe
1               5
```

```
<210> SEQ ID NO 9
<211> LENGTH: 8
<212> TYPE: PRT
<213> ORGANISM: Homo sapiens

<400> SEQUENCE: 9

Lys Gly Gly Phe Ser Phe Arg Phe
1               5

<210> SEQ ID NO 10
<211> LENGTH: 9
<212> TYPE: PRT
<213> ORGANISM: Homo sapiens

<400> SEQUENCE: 10

Lys Lys Gly Gly Phe Ser Phe Arg Phe
1               5

<210> SEQ ID NO 11
<211> LENGTH: 26
<212> TYPE: PRT
<213> ORGANISM: Homo sapiens

<400> SEQUENCE: 11

Thr Ser Gly Pro Leu Gly Asn Leu Ala Glu Glu Leu Asn Gly Tyr Ser
1               5                   10                  15

Arg Lys Lys Gly Gly Phe Ser Phe Arg Phe
            20                  25

<210> SEQ ID NO 12
<211> LENGTH: 375
<212> TYPE: DNA
<213> ORGANISM: Unknown
<220> FEATURE:
<223> OTHER INFORMATION: mouse
<220> FEATURE:
<221> NAME/KEY: CDS
<222> LOCATION: 1..375
<223> OTHER INFORMATION:

<400> SEQUENCE: 12
```

| | | | | | | | | | | | | | | | | |
|---|---|---|---|---|---|---|---|---|---|---|---|---|---|---|---|---|
| atg | agg | ggc | ttc | cgg | cct | ttg | ctt | tcc | cta | ctt | ctc | cct | ctg | agt | gcc | 48 |
| Met | Arg | Gly | Phe | Arg | Pro | Leu | Leu | Ser | Leu | Leu | Leu | Pro | Leu | Ser | Ala | |
| 1 | | | 5 | | | | | 10 | | | | | 15 | | | |
| tgc | ttt | ccc | ctg | ctg | gac | aga | agg | gga | ccc | aca | gac | atc | ggt | gac | atc | 96 |
| Cys | Phe | Pro | Leu | Leu | Asp | Arg | Arg | Gly | Pro | Thr | Asp | Ile | Gly | Asp | Ile | |
| | | | 20 | | | | | 25 | | | | | 30 | | | |
| gga | gcc | agg | atg | aac | tgg | gcc | cag | ctg | gct | gag | gga | cat | ccc | ccc | aac | 144 |
| Gly | Ala | Arg | Met | Asn | Trp | Ala | Gln | Leu | Ala | Glu | Gly | His | Pro | Pro | Asn | |
| | | 35 | | | | | 40 | | | | | 45 | | | | |
| tcg | gtt | caa | aat | cca | cag | cca | cag | gcc | ctg | ctt | gtg | gtg | gcc | agg | gag | 192 |
| Ser | Val | Gln | Asn | Pro | Gln | Pro | Gln | Ala | Leu | Leu | Val | Val | Ala | Arg | Glu | |
| | 50 | | | | | 55 | | | | | 60 | | | | | |
| cag | cag | gcc | tcc | cac | agg | gag | cac | acc | ggc | ttc | cgt | cta | ggg | agg | caa | 240 |
| Gln | Gln | Ala | Ser | His | Arg | Glu | His | Thr | Gly | Phe | Arg | Leu | Gly | Arg | Gln | |
| 65 | | | | | 70 | | | | | 75 | | | | | 80 | |
| gac | ggt | agc | agt | gag | gcc | gca | ggg | ttc | ctg | ccc | gcc | gac | tcg | gag | aag | 288 |
| Asp | Gly | Ser | Ser | Glu | Ala | Ala | Gly | Phe | Leu | Pro | Ala | Asp | Ser | Glu | Lys | |
| | | | | 85 | | | | | 90 | | | | | 95 | | |
| gcc | agc | ggc | cct | ctg | ggg | act | ctg | gca | gag | gag | ctg | agc | agc | tac | agc | 336 |
| Ala | Ser | Gly | Pro | Leu | Gly | Thr | Leu | Ala | Glu | Glu | Leu | Ser | Ser | Tyr | Ser | |
| | | | 100 | | | | | 105 | | | | | 110 | | | |
| cgg | agg | aag | gga | ggc | ttc | agc | ttc | cgc | ttt | gga | cgg | tga | | | | 375 |

Arg Arg Lys Gly Gly Phe Ser Phe Arg Phe Gly Arg
        115                 120

<210> SEQ ID NO 13
<211> LENGTH: 124
<212> TYPE: PRT
<213> ORGANISM: Unknown
<220> FEATURE:
<223> OTHER INFORMATION: mouse

<400> SEQUENCE: 13

Met Arg Gly Phe Arg Pro Leu Leu Ser Leu Leu Leu Pro Leu Ser Ala
1               5                   10                  15

Cys Phe Pro Leu Leu Asp Arg Arg Gly Pro Thr Asp Ile Gly Asp Ile
            20                  25                  30

Gly Ala Arg Met Asn Trp Ala Gln Leu Ala Glu Gly His Pro Pro Asn
        35                  40                  45

Ser Val Gln Asn Pro Gln Pro Gln Ala Leu Leu Val Val Ala Arg Glu
    50                  55                  60

Gln Gln Ala Ser His Arg Glu His Thr Gly Phe Arg Leu Gly Arg Gln
65                  70                  75                  80

Asp Gly Ser Ser Glu Ala Ala Gly Phe Leu Pro Ala Asp Ser Glu Lys
                85                  90                  95

Ala Ser Gly Pro Leu Gly Thr Leu Ala Glu Glu Leu Ser Ser Tyr Ser
            100                 105                 110

Arg Arg Lys Gly Gly Phe Ser Phe Arg Phe Gly Arg
        115                 120

<210> SEQ ID NO 14
<211> LENGTH: 7
<212> TYPE: PRT
<213> ORGANISM: Unknown
<220> FEATURE:
<223> OTHER INFORMATION: mouse

<400> SEQUENCE: 14

Glu His Thr Gly Phe Arg Leu
1               5

<210> SEQ ID NO 15
<211> LENGTH: 7
<212> TYPE: PRT
<213> ORGANISM: Unknown
<220> FEATURE:
<223> OTHER INFORMATION: mouse

<400> SEQUENCE: 15

Gly Gly Phe Ser Phe Arg Phe
1               5

<210> SEQ ID NO 16
<211> LENGTH: 8
<212> TYPE: PRT
<213> ORGANISM: Unknown
<220> FEATURE:
<223> OTHER INFORMATION: mouse

<400> SEQUENCE: 16

Lys Gly Gly Phe Ser Phe Arg Phe
1               5

<210> SEQ ID NO 17
<211> LENGTH: 9

-continued

<212> TYPE: PRT
<213> ORGANISM: Unknown
<220> FEATURE:
<223> OTHER INFORMATION: mouse

<400> SEQUENCE: 17

Arg Lys Gly Gly Phe Ser Phe Arg Phe
1               5

<210> SEQ ID NO 18
<211> LENGTH: 26
<212> TYPE: PRT
<213> ORGANISM: Unknown
<220> FEATURE:
<223> OTHER INFORMATION: mouse

<400> SEQUENCE: 18

Ala Ser Gly Pro Leu Gly Thr Leu Ala Glu Glu Leu Ser Ser Tyr Ser
1               5                   10                  15

Arg Arg Lys Gly Gly Phe Ser Phe Arg Phe
            20                  25

<210> SEQ ID NO 19
<211> LENGTH: 1302
<212> TYPE: DNA
<213> ORGANISM: Unknown
<220> FEATURE:
<223> OTHER INFORMATION: mouse
<220> FEATURE:
<221> NAME/KEY: CDS
<222> LOCATION: (1)..(1302)
<223> OTHER INFORMATION:

<400> SEQUENCE: 19

```
atg cag gcg ctc aac atc acc gcg gag cag ttt tcc cgg ctg ctg agc        48
Met Gln Ala Leu Asn Ile Thr Ala Glu Gln Phe Ser Arg Leu Leu Ser
1               5                   10                  15 gca cac aac ctg act cgg gaa cag ttc att cat cgc tat ggg ctg cga        96
Ala His Asn Leu Thr Arg Glu Gln Phe Ile His Arg Tyr Gly Leu Arg
            20                  25                  30 ccg ctg gtc tac acc ccg gag ctg ccc gcg cgc gct aaa ctg gcc ttt       144
Pro Leu Val Tyr Thr Pro Glu Leu Pro Ala Arg Ala Lys Leu Ala Phe
        35                  40                  45 gcg ctg gct gga gca ctc att ttt gcc ctg gcg ctc ttt ggc aac tct       192
Ala Leu Ala Gly Ala Leu Ile Phe Ala Leu Ala Leu Phe Gly Asn Ser
    50                  55                  60 ctg gtc atc tat gtg gtg acc cgc agc aag gcc atg cac acc gtc acc       240
Leu Val Ile Tyr Val Val Thr Arg Ser Lys Ala Met His Thr Val Thr
65                  70                  75                  80 aac atc ttc atc tgc tct ctg gca ctc agt gat ctg ctc att gcc ttc       288
Asn Ile Phe Ile Cys Ser Leu Ala Leu Ser Asp Leu Leu Ile Ala Phe
                85                  90                  95 ttc tgc atc ccc gtc acg atg ctc cag aac atc tcc gac aag tgg ctg       336
Phe Cys Ile Pro Val Thr Met Leu Gln Asn Ile Ser Asp Lys Trp Leu
            100                 105                 110 ggt ggt gcc ttc atc tgc aag atg gtg ccc ttc gtc cag tcc act gct       384
Gly Gly Ala Phe Ile Cys Lys Met Val Pro Phe Val Gln Ser Thr Ala
        115                 120                 125 gtt gtg acg gaa atc ctc acc atg act tgc atc gct gtt gag agg cac       432
Val Val Thr Glu Ile Leu Thr Met Thr Cys Ile Ala Val Glu Arg His
    130                 135                 140 caa gga ctc atc cat cct ttt aaa atg aag tgg cag tac act acc cga       480
Gln Gly Leu Ile His Pro Phe Lys Met Lys Trp Gln Tyr Thr Thr Arg
145                 150                 155                 160
```

```
agg gct ttc aca atc ttg ggt gtg gtc tgg ttg gca gcc atc atc gta      528
Arg Ala Phe Thr Ile Leu Gly Val Val Trp Leu Ala Ala Ile Ile Val
            165                 170                 175 gga tca ccc atg tgg cac gta caa cgc ctc gag att aag tat gac ttc      576
Gly Ser Pro Met Trp His Val Gln Arg Leu Glu Ile Lys Tyr Asp Phe
        180                 185                 190 ctc tat gag aaa gaa cat gtc tgc tgt ttg gaa gag tgg gcc agc ccc      624
Leu Tyr Glu Lys Glu His Val Cys Cys Leu Glu Glu Trp Ala Ser Pro
            195                 200                 205 atg cac cag aga atc tac acc acc ttc atc ctc gtc atc ctc ttc ctc      672
Met His Gln Arg Ile Tyr Thr Thr Phe Ile Leu Val Ile Leu Phe Leu
        210                 215                 220 ctg ccg ctt gtg gtg atg ctt gtc ctc tac agc aag att ggc tat gaa      720
Leu Pro Leu Val Val Met Leu Val Leu Tyr Ser Lys Ile Gly Tyr Glu
225                 230                 235                 240 ctg tgg atc aag aag aga gtt gga gac agt tca gca ctt cag act atc      768
Leu Trp Ile Lys Lys Arg Val Gly Asp Ser Ser Ala Leu Gln Thr Ile
                245                 250                 255 cac ggg aaa gaa atg tcc aaa ata gcc agg aag aag aag cgg gct gtc      816
His Gly Lys Glu Met Ser Lys Ile Ala Arg Lys Lys Lys Arg Ala Val
            260                 265                 270 gtt atg atg gtg aca gtg gtg gct ctc ttc gct gcg tgc tgg gca cct      864
Val Met Met Val Thr Val Val Ala Leu Phe Ala Ala Cys Trp Ala Pro
        275                 280                 285 ttc cat gtt gtt cac atg atg gtt gag tac agt aac ttt gaa aaa gag      912
Phe His Val Val His Met Met Val Glu Tyr Ser Asn Phe Glu Lys Glu
            290                 295                 300 tat gat gat gtc aca atc aag atg gtt ttt gct gtt gca caa aca att      960
Tyr Asp Asp Val Thr Ile Lys Met Val Phe Ala Val Ala Gln Thr Ile
305                 310                 315                 320 ggc ttt ttc aac tcc atc tgt aat ccc ttt gtg tat gca ttt atg aat     1008
Gly Phe Phe Asn Ser Ile Cys Asn Pro Phe Val Tyr Ala Phe Met Asn
                325                 330                 335 gaa aac ttc aaa aag aat ttt ttg tct gcg gtt tgt tat tgc ata gta     1056
Glu Asn Phe Lys Lys Asn Phe Leu Ser Ala Val Cys Tyr Cys Ile Val
            340                 345                 350 aaa gaa acc ttc tcc cca gga cag aag cct gga aat tct ggg att tca     1104
Lys Glu Thr Phe Ser Pro Gly Gln Lys Pro Gly Asn Ser Gly Ile Ser
        355                 360                 365 atg atg caa aag aga gca aag tta tca cga tca cag cgt cca gtg gcg     1152
Met Met Gln Lys Arg Ala Lys Leu Ser Arg Ser Gln Arg Pro Val Ala
    370                 375                 380 gaa gcc aaa gga gac tta ttc agc gat gcc aac gtt gat gtc aaa ttg     1200
Glu Ala Lys Gly Asp Leu Phe Ser Asp Ala Asn Val Asp Val Lys Leu
385                 390                 395                 400 tgt gag cag cca ggg gag aaa agg caa ctc aag cga cag ctt gcc ttc     1248
Cys Glu Gln Pro Gly Glu Lys Arg Gln Leu Lys Arg Gln Leu Ala Phe
                405                 410                 415 ttt agt tct gaa ctt tct gaa aac tct act ttc ggc agt gga cat gaa     1296
Phe Ser Ser Glu Leu Ser Glu Asn Ser Thr Phe Gly Ser Gly His Glu
            420                 425                 430 ctg taa                                                              1302
Leu

<210> SEQ ID NO 20
<211> LENGTH: 433
<212> TYPE: PRT
<213> ORGANISM: Unknown
<220> FEATURE:
<223> OTHER INFORMATION: mouse
```

<400> SEQUENCE: 20

```
Met Gln Ala Leu Asn Ile Thr Ala Glu Gln Phe Ser Arg Leu Leu Ser
1               5                   10                  15
Ala His Asn Leu Thr Arg Glu Gln Phe Ile His Arg Tyr Gly Leu Arg
            20                  25                  30
Pro Leu Val Tyr Thr Pro Glu Leu Pro Ala Arg Ala Lys Leu Ala Phe
        35                  40                  45
Ala Leu Ala Gly Ala Leu Ile Phe Ala Leu Ala Leu Phe Gly Asn Ser
    50                  55                  60
Leu Val Ile Tyr Val Val Thr Arg Ser Lys Ala Met His Thr Val Thr
65                  70                  75                  80
Asn Ile Phe Ile Cys Ser Leu Ala Leu Ser Asp Leu Leu Ile Ala Phe
                85                  90                  95
Phe Cys Ile Pro Val Thr Met Leu Gln Asn Ile Ser Asp Lys Trp Leu
            100                 105                 110
Gly Gly Ala Phe Ile Cys Lys Met Val Pro Phe Val Gln Ser Thr Ala
        115                 120                 125
Val Val Thr Glu Ile Leu Thr Met Thr Cys Ile Ala Val Glu Arg His
    130                 135                 140
Gln Gly Leu Ile His Pro Phe Lys Met Lys Trp Gln Tyr Thr Thr Arg
145                 150                 155                 160
Arg Ala Phe Thr Ile Leu Gly Val Val Trp Leu Ala Ala Ile Ile Val
                165                 170                 175
Gly Ser Pro Met Trp His Val Gln Arg Leu Glu Ile Lys Tyr Asp Phe
            180                 185                 190
Leu Tyr Glu Lys Glu His Val Cys Cys Leu Glu Glu Trp Ala Ser Pro
        195                 200                 205
Met His Gln Arg Ile Tyr Thr Thr Phe Ile Leu Val Ile Leu Phe Leu
    210                 215                 220
Leu Pro Leu Val Val Met Leu Val Leu Tyr Ser Lys Ile Gly Tyr Glu
225                 230                 235                 240
Leu Trp Ile Lys Lys Arg Val Gly Asp Ser Ser Ala Leu Gln Thr Ile
                245                 250                 255
His Gly Lys Glu Met Ser Lys Ile Ala Arg Lys Lys Lys Arg Ala Val
            260                 265                 270
Val Met Met Val Thr Val Val Ala Leu Phe Ala Ala Cys Trp Ala Pro
        275                 280                 285
Phe His Val Val His Met Met Val Glu Tyr Ser Asn Phe Glu Lys Glu
    290                 295                 300
Tyr Asp Asp Val Thr Ile Lys Met Val Phe Ala Val Ala Gln Thr Ile
305                 310                 315                 320
Gly Phe Phe Asn Ser Ile Cys Asn Pro Phe Val Tyr Ala Phe Met Asn
                325                 330                 335
Glu Asn Phe Lys Lys Asn Phe Leu Ser Ala Val Cys Tyr Cys Ile Val
            340                 345                 350
Lys Glu Thr Phe Ser Pro Gly Gln Lys Pro Gly Asn Ser Gly Ile Ser
        355                 360                 365
Met Met Gln Lys Arg Ala Lys Leu Ser Arg Ser Gln Arg Pro Val Ala
    370                 375                 380
Glu Ala Lys Gly Asp Leu Phe Ser Asp Ala Asn Val Asp Val Lys Leu
385                 390                 395                 400
Cys Glu Gln Pro Gly Glu Lys Arg Gln Leu Lys Arg Gln Leu Ala Phe
```

```
                        405                 410                 415
Phe Ser Ser Glu Leu Ser Glu Asn Ser Thr Phe Gly Ser Gly His Glu
            420                 425                 430
Leu
```

G-PROTEIN COUPLED RECEPTOR LIGANDS AND METHODS

This Application claims the benefit of U.S. Provisional Patent Application No. 60/372,640, filed Apr. 12, 2002, now pending, which is herein incorporated by reference in its entirety.

FIELD OF THE INVENTION

The present invention relates to a G-protein coupled receptor and the identification of ligands that bind to the receptor. More particularly, it relates to methods of using the receptor in screening systems to identify agonists and antagonists of the receptor. The invention also relates to the novel peptide ligands of the receptor, nucleic acids which encode the peptide ligands as well as methods of making and using the peptide ligands.

BACKGROUND OF THE INVENTION

G protein-coupled receptors (GPCRs) mediate cellular responses to an enormous diversity of signaling molecules, including hormones, neurotransmitters, and local mediators, which are as varied in structure as they are in function: the list includes proteins and small peptides, as well as amino acid and fatty acid derivatives.

Despite the chemical and functional diversity of the signaling molecules that bind to them, all of the G protein-coupled receptors whose amino acid sequences are known from DNA sequencing studies have a similar structure and are almost certainly evolutionarily related. They consist of a single polypeptide chain that threads back and forth across the lipid bilayer seven times. The members of this receptor family have conserved not only their amino acid sequence but also their functional relationship to G proteins by means of which they broadcast into the interior of the cell the message that an extracellular ligand is present.

G-protein coupled receptors are an important class of drug targets that exist on the surface membrane of all cells and are associated with a wide range of therapeutic categories, including pain control and analgesia, asthma, inflammation, obesity, cancer, cardiovascular, metabolic, viral, immuno-modulatory, gastrointestinal and central nervous system diseases. There are estimated to be over 1,000 GPCRs in the human genome with potential therapeutic utility. Although, GPCRs have historically been valuable drug targets, to date there are only approximately 200 well-characterized GPCRs with known ligands, of which only about half are currently targets of commercial drugs. The remaining GPCRs, for which a ligand has not been identified, are typically referred to as "orphan GPCRs".

An orphan GPCR of particular interest is the hRUP4 receptor, hereinafter referred to as the SP9155 receptor. The SP9155 receptor also has been referred to as vc-⁻38_1, AXOR16 and as GP103. The amino acid sequence of this receptor has been disclosed previously, for example, in several International Applications including PCT/US99/19351 (WO 00/11015), PCT/US99/24065 (WO 00/22131), PCT/US99/23687 (WO 00/31258), PCT/US00/16869 (WO00/78809), PCT/JP00/05684 (WO 01/16316) and PCT/JP00/09409 (WO 01/48189). However, these publications do not disclose a ligand for the SP9155 receptor. The SP9155 receptor has amino acid sequence homology to orexin A, orexin B and NPFF receptors. Orexin A and B receptors have been shown to be involved in metabolic diseases such as obesity (Shiraishi, et al., (2000) Physiol. Behav. 71:251-61; Mondal, et al., (1999) Neurosci. Lett. 273:45-48 and Dun, et al., (2000) Regul. Pept. 96:65-70). NPFF receptors have been shown to be involved pain control and analgesia (Lake, et al., (1991) Neurosci. Lett. 132:29-32; Kavaliers, et al., (1992) Peptides 13:603-607 and Dong, et al., (2001) Cell 106:619-632). Accordingly, identification of a ligand for the SP9155 receptor would be potentially useful in developing therapies for metabolic and neurological disorders.

Neuropeptides are one therapeutically important class of GPCR ligands which are used as signaling molecules in the nervous system of most organisms, including mammals. For example, RF-amide neuropeptides have been shown to have diverse functions including cardioexcitation (Greenberg, et al., (1979), Am. Zoologist 19:163-167 and Groome, et al., (1994) Biol. Bull. 186:309-318), control of muscle contraction (Bowman, et al., (1996) Peptides 17:381-387 and Franks, et al., (1994) Parasitology 108:229-236), neuromodulation in invertebrates (Brownlee, et al., (1995) Parasitology 111:379-384 and Cottrell, et al., (1983) Nature 304:638-640) as well as anti-opioid effects in vertebrates (Kavaliers, et al., (1985) Neuroendocrinology 40:533-535 and Yang, et al., (1985) Prog. Clin. Biol. Res. 192:313-322). Accordingly, the identification of the GPCRs to which neuropeptides such as RF-amides bind would also be useful in developing potential therapeutics.

SUMMARY OF THE INVENTION

The present inventors have addressed the foregoing needs by identifying the ligand for the orphan GPCR SP9155 which enables methods for screening agonists and antagonists of the receptor. In addition, the present inventors have also identified novel peptide ligands for SP9155 and the cDNA which encodes the SP9155 ligands.

The present invention provides a method for identifying an agonist or antagonist of SP9155 comprising the steps of (a) contacting SP9155 or a functional fragment thereof, in the presence of a known amount of labeled SP9155 ligand, with a sample to be tested for the presence of said agonist or antagonist; and (b) measuring the amount of the ligand specifically bound to the receptor. In the method, the sample is identified as containing an agonist or antagonist by measuring substantially reduced binding of the ligand to the receptor, compared to what would be measured in the absence of the sample. Preferably the ligand is a polypeptide comprising the amino acid sequence of any of SEQ ID NOs: 4-11 or 13-18. Preferably, the polypeptide is amidated at the carboxy-terminus. Preferably, the receptor comprises the amino acid sequence of SEQ ID NO: 2 or SEQ ID NO: 20. Preferably, the source of the SP9155 receptor is a membrane isolated from a mammalian cell expressing the receptor.

The invention also provides a method for identifying an agonist or antagonist of an SP9155 receptor or functional fragment thereof including the step of (a) contacting a cell expressing the receptor in the presence of a known amount of SP9155 ligand, with a sample to be tested for the presence of said agonist or antagonist; and (b) measuring calcium mobilization by the cell. In the method, the sample is identified as containing an antagonist by measuring substantially reduced calcium mobilization, compared to what would be measured in the absence of said sample and the sample is identified as containing an agonist by measuring substantially increased calcium mobilization, compared to what would be measured in the absence of said sample. Preferably, the calcium mobilization by the cell is measured by contacting the calcium with a calcium indicator, such as 1-[2-Amino-5-(2,7-dichloro-6-hydroxy-3-oxy-9-xanthenyl) phenoxy]-2-(2'-amino-5'-methylphenoxy)ethane-N,N,N',N'-tetraacetic acid, pentaacetoxymethyl ester (Fluor-3-AM), and then measuring fluorescence of the indicator. Preferably the ligand is a polypeptide comprising an amino acid sequence of any of SEQ ID NOs: 4-11 or 13-18. Preferably, the polypeptide is amidated at the carboxy-terminus. Preferably the SP9155 receptor comprises the amino acid sequence of SEQ ID NO: 2 or of SEQ ID NO: 20.

The present invention provides an RF-Amide precursor, from both mice and humans, comprising the amino acid and the nucleotide sequences set forth in SEQ ID NOs: 3 and 4 and in SEQ ID NOs: 12 and 13, respectively. The Human and Mouse precursors each include several smaller, internal peptides, preferably antigenic peptides, which, preferably, comprise the amino acid sequence set forth in any of SEQ ID NOs: 5-11 and 12-18. The Human precursor is expressed in brain, heart and liver tissue. Also provided is an isolated, antigenic polypeptide comprising 7 or more contiguous residues of an amino acid sequence selected from SEQ ID NOs: 4 (Human precursor) and 13 (Mouse precursor). In preferred embodiments, the polypeptides are labeled. The polypeptides may comprise an unmodified or modified (e.g., amidated) carboxy-terminus. The invention also includes antibody molecules which specifically bind to the polypeptides of the invention.

The invention also provides an isolated nucleic acid encoding a precursor polypeptide (SEQ ID NO: 4 or SEQ ID NO: 13) which, preferably, comprises the nucleotide sequence set forth in SEQ ID NO: 3 or in SEQ ID NO: 12, respectively. Also provided is an isolated nucleic acid encoding an antigenic polypeptide, preferably an antigenic polypeptide, comprising 7 or more contiguous residues of an amino acid sequence selected from SEQ ID NOs: 4 (Human precursor) and 13 (Mouse precursor). Preferably, the nucleic acid comprises 21 or more contiguous nucleotides from the nucleotide sequence set forth in SEQ ID NO: 3 or in SEQ ID NO: 12.

The invention further provides a recombinant vector comprising the nucleic acids of the invention and a host cell comprising the vector.

The Mouse SP9155 receptor (e.g., SEQ ID NOs: 19 and 20) and any functional fragment thereof is a further part of the present invention along with peptides comprising 7 or more contiguous residues from the amino acid sequence set forth in SEQ ID NO: 20 and nucleic acids which encode the peptides (e.g., nucleic acids comprising 21 or more contiguous nucleotides from the nucleotide sequence set forth in SEQ ID NO: 19).

The invention further provides a method for making a polypeptide of the invention comprising culturing a host cell comprising a vector of the invention under conditions in which the nucleic acid present in the vector is expressed. Preferably, the polypeptide is isolated from the culture.

The present invention also provides a method for binding an antigenic peptide comprising 7 or more contiguous residues of an amino acid sequence selected from SEQ ID NOs: 4 and 13 with an antibody molecule which recognizes the peptide including the step of contacting the peptide with the antibody molecule.

The present invention also provides a method for treating or preventing a medical condition in a subject mediated by the SP9155 receptor including the step of administering, to the subject, a pharmaceutical composition which includes an antibody molecule which recognizes a polypeptide of the invention along with a pharmaceutically acceptable carrier. The method may be used to treat a medical condition such as pain or obesity.

The RF-amide peptides of the invention may be useful, inter alia, for binding and modulating the activity of G-protein Coupled Receptors (GPCRs) such as the Human SP9155 receptor (e.g., SEQ ID NOs: 1 and 2; see also WO 00/11015, WO 00/22131, WO 00/31256, WO 00/78809, WO 01/16316 and WO 01/48189) or the Mouse SP9155 receptor (e.g., SEQ ID NOs: 19 and 20). The Human SP9155 receptor is expressed in brain, heart, kidney and colon tissue. The RF-amide peptides of the invention may also be used as antigenic peptides for the generation of antibody molecules which recognize the human and mouse precursors or any subsequence thereof.

DETAILED DESCRIPTION OF THE INVENTION

Assays

The present invention includes assays for the discovery of agonists and antagonists of the SP9155 receptor or a functional fragment thereof that may be useful in treatment and management of a variety of medical conditions mediated by binding of the receptor to its ligands such as metabolic disorders (e.g., obesity) or CNS conditions (e.g., pain). Specifically, the SP9155 receptor or a functional fragment thereof and RF-amide peptide ligands of this invention can be employed in such screening methods. Essentially, these methods involve contacting an SP9155 receptor (e.g., SEQ ID NO: 2 or SEQ ID NO: 20) or a functional fragment thereof with an SP9155 ligand (e.g., any of SEQ ID NOs: 4-11 and 13-18 or any subsequence thereof) and a sample to be tested for the presence of a SP9155 receptor agonist or antagonist.

"Sample" or "candidate substance" refers to a composition which is evaluated in a test or assay, for example, for the ability to agonize or antagonize the SP9155 receptor (e.g., SEQ ID NO: 2 or SEQ ID NO: 20) or a functional fragment thereof. Samples may include substances including small molecules, peptides, nucleotides, polynucleotides, subatomic particles and radiation (e.g., $\alpha$ particles, $\beta$ particles, $\gamma$ radiation, X-rays) and antibody molecules.

Antagonists and agonists may modulate the ability of the SP9155 receptor (e.g., SEQ ID NO: 2 or SEQ ID NO: 20) or a functional fragment thereof to bind to a ligand such as an RF-Amide peptide (e.g., any of SEQ ID NOs: 4-11 and 13-18 or any subsequence thereof) and/or modulate the ability of the SP9155 receptor or a functional fragment thereof to produce intracellular signals (e.g., G-Protein coupling, calcium mobilization).

Two basic types of screening systems are preferred, a labeled-ligand binding assay and a "functional" assay. A labeled ligand for use in the binding assay can be obtained by labeling SP9155 receptor ligand (e.g., any of SEQ ID NOs: 4-11 and 13-18 or any subsequence thereof) or a known SP9155 receptor agonist or antagonist with a detectable label (e.g., $^{125}H$ or $^{3}H$). Typically, a given amount of an SP9155 receptor of the invention (e.g., SEQ ID NO: 2 or SEQ ID) NO: 20) is contacted with increasing amounts of the labeled ligand (e.g., $^{3}H$-p52), and the amount of the bound, labeled ligand is measured after removing unbound, labeled ligand by washing. As the amount of the labeled ligand is increased, a point is eventually reached at which all receptor binding sites are occupied or saturated. Specific receptor binding of the labeled ligand is abolished by a large excess of unlabeled ligand.

Preferably, an assay system is used in which non-specific binding of the labeled ligand to the receptor is minimal. Non-specific binding is typically less than 50%, preferably less than 15%, and more preferably less than 10% of the total binding of the labeled ligand.

The term "SP9155 receptor ligand" includes RF-Amide peptides of the invention, for example, as set forth in Table 1 (e.g., any of SEQ ID NOs: 4-11 or 13-18) or any analog thereof. The term also includes any peptide comprising 7 or more contiguous amino acids from SEQ ID NO: 4 or from SEQ ID NO: 13 (discussed below). Preferably, the peptide ligands are carboxy-terminally amidated.

In principle, a binding assay of the invention could be carried out using a soluble receptor of the invention, e.g., following production and refolding by standard methods from an E. coli expression system, and the resulting receptor-labeled ligand complex could be precipitated, e.g., using an antibody against the receptor. The precipitate could then be washed and the amount of the bound labeled ligand could be measured.

Preferably, however, a nucleic acid encoding the SP9155 receptor of the invention is transformed or transfected into an appropriate host cell (e.g., HEK293 or CHO), whereby the receptor will become incorporated into the membrane of the cell. A membrane fraction can then be isolated from the cell and used as a source of the receptor for assay. Preferably, specific binding of the labeled ligand to a membrane fraction from the untransfected host cell will be negligible.

The binding assays of this invention can be used to identify both agonists and antagonists of the SP9155 receptor or a functional fragment thereof because, in general, both will modulate the binding of the labeled ligand to the receptor.

In the basic binding assay, the method for identifying an SP9155 receptor agonist or antagonist includes the steps of (a) contacting an SP9155 receptor (e.g., SEQ ID NO: 2, SEQ ID NO: 20 or a functional fragment thereof), in the presence of a known amount of labeled SP9155 receptor ligand (e.g., any of SEQ ID NOs: 4-11 and 13-18 or any subsequence thereof), with a sample; and (b) measuring the amount of the ligand specifically bound to the receptor.

The sample can be identified as containing an agonist or antagonist by measuring substantially reduced binding of the ligand to the receptor, compared to what would be measured in the absence of the sample.

In one embodiment of the invention, the foregoing method includes additional steps which are performed in a separate, control experiment: (c) contacting an SP9155 receptor or functional fragment thereof, in the presence of a known amount of labeled ligand, with a compound known to be an SP9155 receptor agonist or antagonist; and (d) measuring the amount of labeled ligand bound to the receptor.

Cellular or functional assays may also be used to determine if a sample contains an SP9155 receptor agonist or antagonist. In these assays, the ability of a sample to modulate a cellular parameter which is mediated by the SP9155 receptor (e.g., SEQ ID NO: 2 or SEQ ID NO: 20) is evaluated; such parameters include, but are not limited to, intracellular second messenger pathways activated via the receptors, changes in cell growth rate, secretion of hormones, mobilization of calcium, etc., using published methods. Examples of such methods include measurement of the effects of the ligands on receptor-mediated inhibition of forskolin-stimulated intracellular cAMP production (Parker, et al., (1995) Mol. Brain Res. 34:179-189), receptor-stimulated $Ca^{2+}$ mobilization and mitogenic effects (Sethi, et al., (1991) Cancer Res. 51:1674-1679), and inositol phosphate production and MAP kinase induction (Wang, et al., (1998) Biochemistry 37:6711-17. In preferred embodiments, calcium mobilization in cells expressing the SP9155 receptor is determined using a Fluorometric Imaging Plate Reader (FLIPR) assay, for example, as described in Zhang, et al., (2001) Journal of Biol. Chem. 276(11):8608-8615. In general, the FLIPR assay includes the steps of: (a) contacting a cell (e.g., HEK293 cell or CHO cell) expressing an SP9155 receptor (e.g., SEQ ID NO: 2, SEQ ID NO: 20 or a functional fragment thereof), in the presence of a known amount of SP9155 receptor ligand (e.g., any of SEQ ID NOs: 4-11 and 13-18 or any subsequence thereof), with a sample; and (b) measuring calcium mobilization by the cell.

Calcium mobilization can be measured by exposing the cell to a calcium indicator such as Fluor-3-Am (Molecular Probes; Eugene, OR; 1-[2-Amino-5-(2,7-dichloro-6-hydroxy-3-oxy-9phenoxy]-2-(2'-amino-5'-methylphenoxy) ethane-N,N,N',N'-tetraacetic acid, pentaacetoxymethyl ester). In the presence of $Ca^{2+}$, the indicator fluoresces. The fluorescence can be detected by analyzing the cells, for example, with a fluorometric imaging plate reader.

The sample can be identified as containing an antagonist by measuring substantially reduced calcium mobilization, compared to what would be measured in the absence of the sample and the sample can be identified as containing an agonist by measuring substantially increased calcium mobilization, compared to what would be measured in the absence of the sample.

Molecular Biology

The amino acid and nucleotide sequences of polypeptides and nucleic acids of the invention appear in the Sequence Listing as summarized, below, in Table 1.

TABLE 1

Polypeptides and Nucleic Acids of the Invention

| Polypeptide or Polynucleotide | Sequence Identifier |
|---|---|
| Human SP9155-nucleotide sequence | SEQ ID NO:1 |
| Human SP9155-amino acid sequence | SEQ ID NO:2 |
| Human RF-amide peptide precursor-nucleotide sequence | SEQ ID NO:3 |
| Human RF-amide peptide precursor-amino acid sequence | SEQ ID NO:4 |
| Human P51-amino acid sequence *(80-88) †(238-264) | SEQ ID NO:5 |
| Human P242-amino acid sequence *(73-88) †(217-264) | SEQ ID NO:6 |
| Human P552-amino acid sequence *(61-88) †(181-264) | SEQ ID NO:7 |
| Human P52-amino acid sequence *(127-133) †(379-399) | SEQ ID NO:8 |
| Human P513-amino acid sequence *(126-133) †(376-399) | SEQ ID NO:9 |
| Human P517-amino acid sequence *(125-133) †(373-399) | SEQ ID NO:10 |
| Human P518-amino acid sequence *(108-133) †(322-399) | SEQ ID NO:11 |
| Mouse RF-amide peptide precursor-nucleotide sequence | SEQ ID NO:12 |
| Mouse RF-amide peptide precursor-amino acid sequence | SEQ ID NO:13 |
| Mouse P51-amino acid sequence *(71-77) †(211-231) | SEQ ID NO:14 |

TABLE 1-continued

Polypeptides and Nucleic Acids of the Invention

| Polypeptide or Polynucleotide | Sequence Identifier |
|---|---|
| Mouse P52-amino acid sequence *(116-122) †(346-366) | SEQ ID NO:15 |
| Mouse P513-amino acid sequence *(115-122) †(343-366) | SEQ ID NO:16 |
| Mouse P517-amino acid sequence *(114-122) †(340-366) | SEQ ID NO:17 |
| Mouse P518-amino acid sequence *(97-122) †(289-366) | SEQ ID NO:18 |
| Mouse SP9155-nucleotide sequence | SEQ ID NO:19 |
| Mouse SP9155-amino acid sequence | SEQ ID NO:20 |

Typically, the precursors are cleaved, in vivo, at a recognition site, for example by a protease (e.g., a furin protease or prohormone convertase), to yield an RF-Amide peptide which includes carboxy-terminal Arg-Phe (RF) motif. The carboxy-terminus can be subsequently amidated by cellular amidases to create an Arg-Phe—C(=O)—NH$_2$ (RF-amide) motif. Peptides with an amino acid sequence of any of SEQ ID NOs: 4-11 and 13-18 may comprise a free, unmodified carboxy-terminus or, preferably, an amidated carboxy-terminus.

The numbers in parentheses in the SEQ ID NOs: 5-11 rows which are marked by "*" indicate the portion of the human precursor (SEQ ID NO: 4) from which the peptides were derived. Similarly, the numbers in parentheses in the SEQ ID NOs: 14-18 rows which are marked by "*" indicate the portion of the mouse precursor (SEQ ID NO: 13) from which the peptides were derived. The parenthetical numbers marked by "‡" indicate the nucleotides of the corresponding human or mouse precursor gene which encodes the indicated peptide.

Although the nucleotide sequences set forth in SEQ ID NOs: 3 and 12 are deoxyribonucleotides, nucleic acids comprising the corresponding ribonucleotide sequences are also within the scope of the present invention. Nucleic acids which include the anti-sense strand of the SEQ ID NOs: 3 and 12 or any subsequence thereof are also within the scope of the present invention.

Several coding single nucleotide polymorphisms (cSNPs) have been identified in the Human SP9155 gene. Each cSNP (i.e., g154a-G52S; t181g-F61V; t206g-V69G; g208t-V70L; t447g-H149Q; g748t-G250C; t1031c-L344S; c1111t-R371W; g1162a-G388R and c1228t-L410F) is set forth in the Sequence Listing. Furthermore, several cSNPs have been identified in the Human precursor. Each cSNP, which is also set forth in the Sequence Listing, is summarized below in Table 2.

TABLE 2

Coding Single Nucleotide Polymorphisms in Human Precursor

| cSNP (SEQ ID NO:3) | Amino Acid Sequence Variation (SEQ ID NO:4) |
|---|---|
| 76: g or c | 26: Gln or Glu |
| 103: g or a | 35: Arg or Gly |
| 139: c or t | 47: Pro or Ser |
| 203: t or a | 68: His or Leu |
| 239: a or g | 80: Gly or Glu |

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

For the purposes of the present invention, the term "RF-Amide" or "RF-Amide peptide" or "RF-Amide polypeptide" includes any peptide of the invention (e.g., see Table 1) or any analog thereof which is in any form. For example, the term includes peptides with an amidated carboxy-terminus and peptides with an unmodified carboxy-terminus.

The term "SP9155" or "SP9155 receptor" includes the Human receptor (e.g., SEQ ID NOs: 1 and 2) and the Mouse receptor (e.g., SEQ ID NOs: 19 and 20).

The term "subject" or "patient" refers to any organism, preferably an animal, more preferably a mammal (e.g., mouse, rat, rabbit, cow, dog, cat, cow, chimpanzee, gorilla) and most preferably a human.

The present invention includes recombinant versions of the RF-amide peptides of the invention. The term "recombinant" may describe two or more nucleic acids or proteins which are not naturally contiguous and which are fused to each other. The term may also refer to a nucleic acid or protein which has been altered (e.g., post-translationally modified or mutated) by human intervention. For example, a wild-type codon may be replaced with a redundant codon encoding the same amino acid residue or a conservative substitution, while at the same time introducing or removing a nucleic acid sequence recognition site. Similarly, nucleic acid segments encoding desired functions may be fused to generate a single genetic entity encoding a desired combination of functions not found together in nature. Although restriction enzyme recognition sites are often the targets of such artificial manipulations, other site-specific targets, e.g., promoters, DNA replication sites, regulation sequences, control sequences, or other useful features may be incorporated by design. Sequences encoding epitope tags for detection or purification, as described below, may also be incorporated.

A "polynucleotide sequence", "nucleic acid sequence" or "nucleotide sequence" is a series of two or more nucleotide bases (also called "nucleotides") in a nucleic acid, such as DNA or RNA.

The present invention includes nucleic acid fragments of any of the polynucleotides set forth in Table 1 (e.g., SEQ ID NO: 3 or 12). A nucleic acid "fragment" includes at least about 12, 15, 18 or 21 (e.g., 22, 23 or 24), generally at least about 25 (e.g., 26, 27, 28, 29, 30, 31, 32, 33 or 34), preferably at least about 35 (e.g., 36, 37, 38, 39, 40, 41, 42, 43 or 44), more preferably at least about 45 (e.g., 46, 47, 48, 49, 50, 51, 52, 53 or 54), and most preferably at least about 55 or more contiguous nucleotides (e.g. ,56, 57, 58, 59, 60, 100, 200, 300, 400, 500, 1000 or 1200) from, for example, any of SEQ ID NOs: 3 and 12.

Short nucleic acid fragments (e.g., between about 10 nucleotides and about 100 nucleotides) may also be referred to as "oligonucleotides". Oligonucleotides can be used as primers for PCR amplification. "Amplification" of DNA as used herein may denote the use of polymerase chain reaction (PCR) to increase the concentration of a particular DNA sequence within a mixture of DNA sequences. For a description of PCR see Saiki, et al., (1988) Science 239:487. Oligonucleotides and nucleic acid fragments can be labeled, e.g., by incorporation of $^{32}$P-nucleotides, $^{3}$H-nucleotides, $^{14}$C-nucleotides, $^{35}$S-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids. Generally, oligonucleotides are prepared synthetically, preferably on a nucleic acid synthesizer.

A "protein sequence", "peptide sequence" or "polypeptide sequence" or "amino acid sequence" may refer to a series of two or more amino acids in a protein, peptide or polypeptide.

"Protein", "peptide" or "polypeptide" includes a contiguous string of amino acids. Preferred peptides of the invention include those set forth in Table 1 as well as variants (e.g., carboxy-terminally amidated variants) and fragments thereof. Such fragments preferably comprise at least about 4, 5, 6 or 7 (e.g., 8, 9, 10 or 11), preferably at least about 12 (e.g.,13, 14, 15, 16, 17, 18 or 19), more preferably at least about 20 (e.g., 21, 22, 23, 24, 25, 26, 27, 28 or 29), and most preferably at least about 30 (e.g., 31, 32, 33, 34, 35, 36, 37, 38, 39, 40, 50, 60, 70, 80, 90, 100, 124 or 136) or more contiguous amino acid residues from any of SEQ ID NOs: 4 and 13. As discussed below, such peptides may be useful as antigens for generating antibody molecules which recognize the RF-Amide peptide precursor peptides (e.g., SEQ ID NOs: 4 and 13) or any fragments thereof.

The polypeptides of the invention can be produced by proteolytic cleavage of an intact peptide, by chemical synthesis or by the application of recombinant DNA technology and are not limited to polypeptides delineated by proteolytic cleavage sites. The polypeptides, either alone or cross-linked or conjugated to a carrier molecule to render them more immunogenic, are useful as antigens to elicit the production of antibodies and fragments thereof. The antibodies can be used, e.g., in immunoassays for immunoaffinity purification, etc.

The term "isolated nucleic acid" or "isolated polypeptide" may refer to a nucleic acid, such as an RNA or DNA molecule or a mixed polymer, or to a polypeptide, respectively, which is partially or fully separated from other components that are normally found in cells or in recombinant DNA expression systems. These components include, but are not limited to, cell membranes, cell walls, ribosomes, polymerases, serum components, and flanking genomic sequences. The term thus includes a nucleic acid that has been removed from its naturally occurring environment, and may include recombinant or cloned DNA isolates and chemically synthesized analogs or analogs biologically synthesized by heterologous systems.

An isolated nucleic acid or polypeptide will, preferably, be an essentially homogeneous composition of molecules but may contain some heterogeneity.

The term "substantially pure" may refer to an RF-amide peptide, nucleic acid or other material that is free from other contaminating proteins, nucleic acids, and other biologicals derived from an original source organism or recombinant DNA expression system. Purity may be assayed by standard methods and will typically exceed at least about 50%, preferably at least about 75%, more preferably at least about 90%, and most preferably at least about 95% (e.g., about 100%) purity. Purity evaluation may be made on a mass or molar basis.

The invention further encompasses proteins and nucleic acids having, respectively, amino acid or nucleotide sequences which bear sequence identity or similarity to the proteins and nucleic acids set forth in Table 1. Sequence "identity" refers to exact matches between the nucleotides or amino acids of two sequences which are being compared. Sequence "similarity" or "homology" refers to both exact matches between the amino acids of two polypeptides which are being compared in addition to matches between non-identical, biochemically related amino acids. Biochemically related amino acids share similar properties and may be interchangeable. Amino acids with similar properties which may be interchangeable are well known in the art. For example, polar/hydrophilic amino acids which may be interchangeable include asparagine, glutamine, serine, cysteine, threonine, lysine, arginine, histidine, aspartic acid and glutamic acid; nonpolar/hydrophobic amino acids which may be interchangeable include glycine, alanine, valine, leucine, isoleucine, proline, tyrosine, phenylalanine, tryptophan and methionine; acidic amino acids which may be interchangeable include aspartic acid and glutamic acid and basic amino acids which may be interchangeable include histidine, lysine and arginine.

Sequence "identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., et al. (1988), SIAM *J. Applied Math.*, 48:1073. Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., (1984) Nucleic Acids Research 12 (1):387), BestFit, BLASTP, BLASTN, and FASTA (Altschul, S. F., et al., (1990) J. Mol. Biol. 215:403-410. The BLASTX program is publicly available from NCBI and other sources (*BLAST Manual*, Altschul, S., et al., NCBI NLM NIH Bethesda, Md. 20894; Altschul, S., et al., (1990) J. Mol. Biol. 215:403-410. The well-known Smith Waterman algorithm may also be used to determine identity.

Preferred parameters for polypeptide sequence comparison include the following:

1) Algorithm: Needleman, et al., (1970), J. Mol. Biol. 48:443-453

Comparison matrix: BLOSSUM62 from Hentikoff, et al., (1992) Proc. Natl Acad. Sci. USA. 89:10915-10919

Gap Penalty: 12

Gap Length Penalty: 4

A program useful with these parameters is publicly available as the "gap" program from Genetics Computer Group, located in Madison, Wis. The aforementioned parameters are the default parameters for peptide comparisons (along with no penalty for end gaps).

Preferred parameters for polynucleotide comparison, using the gap program, include the following:
1) Algorithm: Needleman, et al., (1970) J. Mol. Biol. 48:443-453
Comparison matrix: matches=+10, mismatch =0
Gap Penalty: 50
Gap Length Penalty: 3

The present invention includes nucleic acids (e.g., SEQ ID NOs: 3 and 12) which encode the polypeptides described in Table I (e.g., SEQ ID NOs: 4-11 and 13-18), fragments thereof (discussed supra) as well as nucleic acids which hybridize thereto. Preferably, the nucleic acids hybridize under low stringency conditions, more preferably under moderate stringency conditions and most preferably under high stringency conditions. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook, et al., supra). The conditions of temperature and ionic strength determine the "stringency" of the hybridization. Typical, low stringency, hybridization conditions may be 55° C., 5×SSC, 0.1% SDS, 0.25% milk, and no formamide; or 30% formamide, 5×SSC, 0.5% SDS. Typical, moderate stringency hybridization conditions are similar to the low stringency conditions except the hybridization is carried out in 40% formamide, with 5× or 6×SSC. High stringency hybridization conditions are similar to low stringency conditions except the hybridization conditions may be carried out in 50% formamide, 5× or 6×SSC and, optionally, at a higher temperature (e.g., 57° C., 59° C., 60° C., 62° C., 63° C., 65° C. or 68° C. Typically, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. Typical, selective hybridization conditions occur when there is at least about 55% identity over a stretch of at least about 30 nucleotides, preferably at least about 65% over at least about 25 nucleotides, more preferably at least about 75% to about 95%, or more, over about 20 nucleotides or more. For hybrids of greater than 100 nucleotides in length, equations for calculating the melting temperature have been derived (see Sambrook, et al., supra, 9.50-9.51). For hybridization with shorter nucleic acids, i.e., oligonucleotides, the position of mismatches becomes more important, and the length of the oligonucleotide determines its specificity (see Sambrook, et al., supra, 11.7-11.8).

A further indication that two nucleic acids which encode two polypeptides are substantially identical is that the polypeptide encoded by the first nucleic acid is immunologically cross reactive with the polypeptide encoded by the second nucleic acid. Typically, a polypeptide is regarded as substantially identical to a second polypeptide, for example, where the two peptides differ, primarily, by conservative substitutions.

Also included in the present invention are nucleic acids comprising nucleotide sequences and polypeptides comprising amino acid sequences which are at least about 70% identical, preferably at least about 80% identical, more preferably at least about 90% identical and most preferably at least about 95% identical (e.g., 95%, 96%, 97%, 98%, 99%, 100%) to the reference nucleotide and amino acid sequences of Table 1. Polypeptides comprising amino acid sequences which are at least about 70% similar or identical, preferably at least about 80% similar or identical, more preferably at least about 90% similar or identical and most preferably at least about 95% similar or identical (e.g., 95%, 96%, 97%, 98%, 99%, 100%) to the reference amino acid sequences of Table 1 (e.g., SEQ ID NOs: 4-11 and 13-18) are also included in the present invention. Furthermore, the present invention includes nucleic acids which encode polypeptides comprising amino acid sequences which are at least about 70% similar or identical, preferably at least about 80% similar or identical, more preferably at least about 90% similar or identical and most preferably at least about 95% identical or similar (e.g., 96%, 97%, 98%, 99%, 100%) to those set forth in Table I (e.g., SEQ ID NOs: 4-11 and 13-18).

Some of the physical variants have substantial amino acid sequence homology with the amino acid sequences of the RF-amide peptides of the invention. In this invention, amino acid sequence homology, or sequence identity may be determined by optimizing residue matches and, if necessary, by introducing gaps as required. Homologous amino acid sequences are typically intended to include natural allelic, polymorphic and interspecies variations in each respective sequence. Typical, homologous proteins or peptides will have from about 25-100% homology (if gaps can be introduced) to about 50-100% homology (if conservative substitutions are included), with the amino acid sequence of the RF-amide peptides. Observed homologies will typically be at least about 35%, preferably at least about 50%, more preferably at least about 75%, and most preferably at least about 80% or more. See Needleham, (1970) et al., J. Mol. Biol. 48:443-453; Sankoff, et al., in *Time Warps, String Edits, and Macromolecules: The Theory and Practice of Sequence Comparison,* 1983, Addison-Wesley, Reading, Mass.; and software packages from IntelliGenetics, Mountain View, Calif., and the University of Wisconsin Genetics Computer Group, Madison, Wis.

Nucleic acids encoding the RF-amide peptides or fragments thereof can be prepared by standard methods. For example, DNA can be chemically synthesized using, e.g., the phosphoramidite solid support method of Matteucci, et al., (1981) (J. Am. Chem. Soc. 103:3185), the method of Yoo, et al., (1989) (J. Biol. Chem. 764:17078), or other well known methods. This can be done by sequentially linking a series of oligonucleotide cassettes comprising pairs of synthetic oligonucleotides, as described below.

Of course, due to the degeneracy of the genetic code, many different nucleotide sequences can encode the RF-amide peptides of the invention. The codons can be selected for optimal expression in prokaryotic or eukaryotic systems. Such degenerate variants are, of course, also encompassed by this invention. Moreover, nucleic acids encoding the RF-amide peptides of the invention can readily be modified by nucleotide substitutions, nucleotide deletions, nucleotide insertions, and inversions of nucleotide stretches. Such modifications may result in novel DNA sequences that encode antigens having immunogenic or antigenic activity in common with the wild-type peptides. These modified sequences can be used to produce wild-type or mutant peptides, or to enhance expression in a recombinant DNA system.

The nucleic acids of the invention may be operably linked to DNA segments that control transcription (e.g., promoters; discussed infra), translation (e.g., Kozak sequences (Kozak (1991) J. Biol. Chem. 255:19867-19870 or Kozak (1991) J. Cell. Biol.115:887-903), and/or DNA replication (e.g., origins of replication such as ori).

A nucleic acid is "under the control of", "functionally associated with", "operably linked to" or "operably associated with" transcriptional and/or translational control sequences when the sequences direct RNA polymerase mediated transcription of the coding sequence into RNA, preferably mRNA, which then may be RNA spliced (if it contains introns) and, optionally, translated into a protein encoded by the coding sequence.

The terms "express" and "expression" may mean allowing or causing the information in a gene, RNA or DNA sequence to become manifest; for example, producing a protein by activating the cellular functions involved in transcription and translation of a corresponding gene. Alternatively, a gene may be expressed in vitro; DNA containing the gene may be transcribed by a recombinant RNA polymerase and, optionally, translated, for example, with a rabbit reticulocyte lysate (Promega Corporation; Madison, Wis.). A DNA sequence is expressed in or by a cell, or in vitro, to form an "expression product" such as an RNA (e.g., mRNA) or a protein. The expression product itself may also be said to be "expressed".

Vectors into which the nucleic acids of the invention may be inserted include microbial plasmids, viruses, bacteriophage, integratable DNA fragments, and other vehicles that may facilitate introduction of the nucleic acids into the genome of the host. Plasmids are the most commonly used form of vector but all other forms of vectors which serve a similar function and which are, or become, known in the art are suitable for use herein. See, e.g., Pouwels, et al., *Cloning Vectors: A Laboratory Manual*, 1985 and Supplements, Elsevier, N. Y., and Rodriguez et al. (eds.), *Vectors: A Survey of Molecular Cloning Vectors and Their Uses*, 1988, Buttersworth, Boston, Mass.

Insertion of the DNA encoding the RF-amide peptides or encoding the SP9155 receptor or a functional fragment thereof into a vector is easily accomplished when the termini of both the DNA and the vector comprise compatible restriction sites. If this cannot be done, it may be necessary to modify the termini of the DNA and/or the vector by digesting back single-stranded DNA overhangs generated by restriction endonuclease cleavage to produce blunt ends, or to achieve the same result by filling in the single-stranded termini with an appropriate DNA polymerase (e.g., Klenow). Alternatively, desired sites may be produced, e.g., by ligating nucleotide sequences (linkers) onto the termini. Such linkers may comprise specific oligonucleotide sequences that define desired restriction sites. Restriction sites can also be generated by the use of the polymerase chain reaction (PCR). See, e.g., Saiki, et al., Science 239: 487 (1988). The cleaved vector and the DNA fragments may also be modified if required by homopolymeric tailing.

Recombinant expression vectors used in this invention are typically self-replicating DNA or RNA constructs comprising nucleic acids encoding the RF-amide peptides or encoding the SP9155 receptor or a functional fragment thereof and are usually operably linked to suitable genetic control elements that are capable of regulating expression of the nucleic acids in compatible host cells. Genetic control elements may include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Promoters which may be used to control gene expression include, but are not limited to, the tryptophan (trp) promoter system (Goeddel, et al., (1980) Nucleic Acids Res. 8:4057), the lambda $P_L$ promoter system (Shimatake, et al., (1981) Nature 292:128), cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., Cell (1980) 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296: 39-42), the β-lactamase promoter (Villa-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; promoter elements from yeast or other fungi such as the Gal4 promoter, the ADC (alcohol dehydrogenase) promoter, PGK (phosphoglycerol kinase) promoter or the alkaline phosphatase promoter may also be operably linked to the nucleic acids of the invention. Expression vectors also may contain an origin of replication that allows the vector to replicate independently of the host cell.

The term "host cell" may mean any cell of any organism that is selected, modified, transfected, transformed, grown, or used or manipulated in any way, for the production of a substance by the cell, for example the expression or replication, by the cell, of a gene, a DNA or RNA molecule, a vector, a protein or an enzyme. Preferred host cells include bacterial cells such as *E. coli* (e.g., BL21(DE3), DH5 or HB101) and eukaryotic cells (e.g., HEK293 cells or CHO cells).

The term "transformation" may refer to the introduction of a nucleic acid (e.g., SEQ ID NO: 3 or 12, a fragment thereof, or a nucleic acid which encodes any of SEQ ID NOs: 4-11 and 13-18 or any fragment thereof) into a cell. The introduced gene or sequence may be called a "clone". A host cell that receives the introduced DNA or RNA has been "transformed" and is a "transformant" or is a "clone". The DNA or RNA introduced to a host cell can come from any source, including cells of the same genus or species as the host cell, or cells of a different genus or species.

Expression of nucleic acids encoding the RF-amide peptides of this invention can be carried out by conventional methods in either prokaryotic or eukaryotic cells. Although *E. coli* host cells are employed most frequently in prokaryotic systems, many other bacteria, such as various strains of Pseudomonas and Bacillus, are known in the art and can be used as well. Suitable host cells for expressing nucleic acids encoding the RF-amide peptides or the SP9155 receptor or a functional fragment thereof include prokaryotes and higher eukaryotes. Prokaryotes include both gram-negative and gram-positive organisms, e.g., *E. coli* and *B. subtilis*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. A representative vector for amplifying DNA is pBR322 or many of its derivatives (e.g., pUC 18 or 19). Vectors that can be used to express the RF-amide peptides include, but are not limited to, those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al., "Expression Vectors Employing Lambda-, trp-, lac-, and Ipp-derived Promoters", in Rodriguez and Denhardt (eds.) *Vectors: A Survey of Molecular Cloning Vectors and Their Uses*, 1988, Buttersworth, Boston, pp. 205-236. The peptides of the invention may be expressed at high levels in an *E. coli*/T7 expression system as disclosed in U.S. Pat. Nos. 4,952,496, 5,693,489 and 5,869,320 and in Davanloo, P., et al., (1984) Proc. Natl. Acad. Sci. USA 81: 2035-2039; Studier, F. W., et al., (1986) J. Mol. Biol. 189: 113-130; Rosenberg, A. H., et al., (1987) Gene 56: 125-135; and Dunn, J. J., et al., (1988) Gene 68: 259.

Higher eukaryotic tissue culture cells may also be used for the recombinant production of the RF-amide peptides of the invention. Although any higher eukaryotic tissue culture cell line might be used, including insect baculovirus expression systems, mammalian cells are preferred. Transformation or transfection and propagation of such cells have become a routine procedure. Examples of useful cell lines include Human Embryonic Kidney (HEK293) cells, HeLa cells, chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites, a polyadenylation site, and/or a transcription termination site. These vectors also usually contain a selection gene or amplification gene. Suitable expression vectors may be plasmids, viruses, or retroviruses carrying promoters derived, e.g., from such sources as adenovirus, SV40, parvoviruses, vaccinia virus, or cytomegalovirus. Representative examples of suitable expression vectors include pCR®3.1, pcDNA1, pCD (Okayama, et al., (1985) Mol. Cell Biol. 5:1136), pMClneo Poly-A (Thomas, et al., (1987) Cell 51:503), pREP8, pSVSPORT and derivatives thereof, and baculovirus vectors such as pAC373 or pAC610.

The present invention also includes fusions which include the polypeptides and polynucleotides of the present invention and a second polypeptide or polynucleotide moiety, which may be referred to as a "tag". The fusions of the present invention may comprise any of the polynucleotides or polypeptides set forth in Table 1 or any subsequence or fragment thereof. The fused polypeptides of the invention may be conveniently constructed, for example, by insertion of a polynucleotide of the invention or fragment thereof into an expression vector as described above. The fusions of the invention may include tags which facilitate purification or detection. Such tags include glutathione-S-transferase (GST), hexahistidine (His6) tags, maltose binding protein (MBP) tags, haemagglutinin (HA) tags, cellulose binding protein (CBP) tags and myc tags. Detectable labels or tags such as $^{32}P$, $^{35}S$, $^{14}C$, $^{3}H$, $^{99m}Tc$, $^{111}In$, $^{68}Ga$, $^{18}F$, $^{125}I$, $^{131}I$, $^{113}In$, $^{76}Br$, $^{67}Ga$, $^{99m}Tc$, $^{123}I$, $^{111}In$ and $^{68}Ga$ may also be used to label the polypeptides of the invention. Methods for constructing and using such fusions are very conventional and well known in the art.

Modifications (e.g., post-translational modifications) that occur in a polypeptide often will be a function of how it is made. For polypeptides made by expressing a cloned gene in a host, for instance, the nature and extent of the modifications, in large part, will be determined by the host cell's post-translational modification capacity and the modification signals present in the polypeptide amino acid sequence. For instance, as is well known, glycosylation often does not occur in bacterial hosts such as *E. coli*. Accordingly, when glycosylation is desired, a polypeptide can be expressed in a glycosylating host, generally a eukaryotic cell. Insect cells often carry out post-translational glycosylations which are similar to those of mammalian cells. For this reason, insect cell expression systems have been developed to express, efficiently, mammalian proteins having native patterns of glycosylation. Alternatively, deglycosylation enzymes can be used to remove carbohydrates attached during production in eukaryotic expression systems.

Other modifications may also include addition of amides or aliphatic esters to the polypeptide carboxyl-terminus. The present invention also includes analogs of the RF-amide peptides which contain modifications, such as incorporation of unnatural amino acid residues, or phosphorylated amino acid residues such as phosphotyrosine, phosphoserine or phosphothreonine residues. Other potential modifications include sulfonation, biotinylation, or the addition of other moieties, particularly those that have molecular shapes similar to phosphate groups.

The peptides of the invention may also be cyclized. Specifically, the amino- and carboxy-terminal residues in a peptide or two internal residues of a peptide of the invention can be fused to create a cyclized peptide. Preferably, cyclization is performed such that the carboxy-terminus of the peptide is free. Peptides may also be cyclized such that the amino-terminus is free. Methods for cyclizing peptides are conventional and very well known in the art; for example see Gurrath, et al., (1992) Eur. J. Biochem 210: 911-921.

The RF-amide peptides of the invention may be appended with a polymer which increases the half-life of the peptide in the body of a subject. Preferred polymers include polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG).

It will be appreciated that the same type of modification may be present in the same or varying degrees at several sites in a given polypeptide. Also, a given polypeptide may contain many types of modifications.

Analogs of the RF-amide peptides of the invention can be prepared by chemical synthesis or by using site-directed mutagenesis (Gillman, et al., (1979) Gene 8:81; Roberts, et al., (1987) Nature, 328:731 or Innis (Ed.), 1990, *PCR Protocols: A Guide to Methods and Applications*, Academic Press, New York, N. Y. or the polymerase chain reaction method PCR; Saiki, et al., (1988) Science 239:487, as exemplified by Daugherty, et al., (1991) (Nucleic Acids Res. 19:2471) to modify nucleic acids encoding the peptides. Adding epitope tags for purification or detection of recombinant products is envisioned.

Still other analogs are prepared by the use of agents known in the art for their usefulness in cross-linking proteins through reactive side groups. Preferred derivatization sites with cross-linking agents are free amino or carboxy groups, carbohydrate moieties and cysteine residues.

The term "polypeptide", "peptide" and "protein" encompasses all such modifications, particularly those that are present in polypeptides synthesized by expressing a polynucleotide in a host cell.

Protein Purification

Typically, the peptides of the invention may be produced by expressing a nucleic acid which encodes the polypeptide in a host cell which is grown in a culture (e.g., liquid culture such as luria broth). For example, the nucleic acid may be part of a vector (e.g., a plasmid) which is present in the host cell. Following expression, the peptides of the invention can be isolated from the cultured cells. The peptides of this invention can be purified by standard methods, including, but not limited to, salt or alcohol precipitation, affinity chromatography (e.g., used in conjunction with a purification tagged peptide as discussed above), preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are very well known in the art and are disclosed, e.g., in "*Guide to Protein Purification*", *Methods in Enzymology*, Vol. 182, M. Deutscher, Ed., 1990. Academic Press, New York, N. Y.

Purification steps can be followed by carrying out assays for receptor binding activity as described below. Particularly where an RF-amide peptide is being isolated from a cellular or tissue source, it is preferable to include one or more inhibitors of proteolytic enzymes is the assay system, such as phenylmethanesulfonyl fluoride (PMSF), Pefabloc S.C., pepstatin, leupeptin, chymostatin and EDTA.

Antibody Molecules

Antigenic (i.e., immunogenic) fragments of the RF-amide peptides of the invention, which may or may not bind to the SP9155 or a functional fragment thereof, are within the scope of the present invention. The antigenic peptides may be useful for preparing antibody molecules which recognize the RF-amide peptide precursor or any fragment thereof.

Although it is not always necessary, when RF-amide peptides are used as antigens to elicit antibody production in an immunologically competent host, smaller antigenic fragments are preferably first rendered more immunogenic by cross-linking or concatenation, or by coupling to an immunogenic carrier molecule (i.e., a macromolecule having the property of independently eliciting an immunological response in a host animal, such as diptheria toxin or tetanus). Cross-linking or conjugation to a carrier molecule may be required because small polypeptide fragments sometimes act as haptens (molecules which are capable of specifically binding to an antibody but incapable of eliciting antibody production, i.e., they are not immunogenic). Conjugation of such fragments to an immunogenic carrier molecule renders them more immunogenic through what is commonly known as the "carrier effect".

Carrier molecules include, e.g., proteins and natural or synthetic polymeric compounds such as polypeptides, polysaccharides, lipopolysaccharides, etc. Protein carrier molecules are especially preferred, including, but not limited to, keyhole limpet hemocyanin and mammalian serum proteins such as human or bovine gammaglobulin, human, bovine or rabbit serum albumin, or methylated or other derivatives of such proteins. Other protein carriers will be apparent to those skilled in the art. Preferably, the protein carrier will be foreign to the host animal in which antibodies against the fragments are to be elicited.

Covalent coupling to the carrier molecule can be achieved using methods well known in the art; the exact choice of which will be dictated by the nature of the carrier molecule used. When the immunogenic carrier molecule is a protein, the fragments of the invention can be coupled, e.g., using water-soluble carbodiimides such as dicyclohexylcarbodiimide or glutaraldehyde.

Coupling agents, such as these, can also be used to cross-link the fragments to themselves without the use of a separate carrier molecule. Such cross-linking into aggregates can also increase immunogenicity. Immunogenicity can also be increased by the use of known adjuvants, alone or in combination with coupling or aggregation.

Adjuvants for the vaccination of animals include, but are not limited to, Adjuvant 65 (containing peanut oil, mannide monooleate and aluminum monostearate); Freund's complete or incomplete adjuvant; mineral gels such as aluminum hydroxide, aluminum phosphate and alum; surfactants such as hexadecylamine, octadecylamine, lysolecithin, dimethyldioctadecylammonium bromide, N,N-dioctadecyl-N',N'-bis (2-hydroxymethyl) propanediamine, methoxyhexadecylglycerol and pluronic polyols; polyanions such as pyran, dextran sulfate, poly IC, polyacrylic acid and carbopol; peptides such as muramyl dipeptide, dimethylglycine and tuftsin; and oil emulsions. The polypeptides could also be administered following incorporation into liposomes or other microcarriers.

Information concerning adjuvants and various aspects of immunoassays are disclosed, e.g., in the series by P. Tijssen, *Practice and Theory of Enzyme Immunoassays,* 3rd Edition, 1987, Elsevier, N. Y. Other useful references covering methods for preparing polyclonal antisera include *Microbiology,* 1969, Hoeber Medical Division, Harper and Row; Landsteiner, *Specificity of Serological Reactions,* 1962, Dover Publications, New York, and Williams, et al., *Methods in Immunology and Immunochemistry*, Vol. 1, 1967, Academic Press, New York.

The anti-RF-Amide peptide "antibody molecules" of the invention include, but are by no means not limited to, anti-RF-Amide peptide antibodies (e.g., monoclonal antibodies, polyclonal antibodies, bispecific antibodies and anti-idiotypic antibodies) and fragments, preferably antigen-binding fragments or functional fragments, thereof, such as Fab antibody fragments, F(ab)$_2$ antibody fragments, Fv antibody fragments (e.g., V$_H$ or V$_L$), single chain Fv antibody fragments and dsFv antibody fragments. Furthermore, the antibody molecules of the invention may be fully human antibodies, mouse antibodies. rabbit antibodies, chicken antibodies, human/mouse chimeric antibodies or humanized antibodies.

The anti-RF-amide peptide antibody molecules of the invention preferably recognize human or mouse RF-amide peptides of the invention; however, the present invention includes antibody molecules which recognize RF-amide peptides from different species, preferably mammals (e.g., rat, rabbit, sheep or dog). The present invention also includes complexes comprising the RF-amides peptides of the invention and one or more antibody molecules. Such complexes can be made by simply contacting the antibody molecule with its cognate peptide.

Various methods may be used to make the antibody molecules of the invention. In preferred embodiments, the antibodies of the invention are produced by methods which are similar to those disclosed in U.S. Pat. Nos. 5,625,126; 5,877,397; 6,255,458; 6,023,010 and 5,874,299. Hybridoma cells which produce monoclonal, fully human anti-RF-amide peptide antibodies may then be produced by methods which are commonly known in the art. These methods include, but are not limited to, the hybridoma technique originally developed by Kohler, et al., (1975) (Nature 256: 495-497), as well as the trioma technique (Hering, et al., (1988) Biomed. Biochim. Acta. 47:211-216 and Hagiwara, et al., (1993) Hum. Antibod. Hybridomas 4:15), the human B-cell hybridoma technique (Kozbor, et al., (1983) Immunology Today 4:72 and Cote, et al., (1983) Proc. Natl. Acad. Sci. U.S.A 80:2026-2030), and the EBV-hybridoma technique (Cole, et al., in *Monoclonal Antibodies and Cancer*

*Therapy*, Alan R. Liss, Inc., pp. 77-96, 1985). Again, ELISA may be used to determine if hybridoma cells are expressing anti-RF-amide peptide antibodies.

The anti-RF-amide peptide antibody molecules of the present invention may also be produced recombinantly (e.g., in an *E. coli*/T7 expression system as discussed above). In this embodiment, nucleic acids encoding the antibody molecules of the invention (e.g., $V_H$ or $V_L$) may be inserted into a pet-based plasmid and expressed in the *E. coli*/T7 system. There are several methods by which to produce recombinant antibodies which are known in the art. One example of a method for recombinant production of antibodies is disclosed in U.S. Pat. No. 4,816,567.

The term "monoclonal antibody" includes an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Monoclonal antibodies are advantageous in that they may be synthesized by a hybridoma culture, essentially uncontaminated by other immunoglobulins. The modifier "monoclonal" indicates the character of the antibody as being among a substantially homogeneous population of antibodies, and is not to be construed as requiring production of the antibody by any particular method. As mentioned above, the monoclonal antibodies to be used in accordance with the present invention may be made by the hybridoma method as described by Kohler, et al., (1975) Nature 256: 495.

The term "polyclonal antibody" includes an antibody which was produced among or in the presence of one or more other, non-identical antibodies. In general, polyclonal antibodies are produced from a B-lymphocyte in the presence of several other B-lymphocytes which produced non-identical antibodies. Usually, polyclonal antibodies are obtained directly from an immunized animal.

A "bispecific antibody" comprises two different antigen binding regions which bind to distinct antigens. Bispecific antibodies, as well as methods of making and using the antibodies, are conventional and very well known in the art.

Anti-idiotypic antibodies or anti-idiotypes are antibodies directed against the antigen-combining region or variable region (called the idiotype) of another antibody molecule. As disclosed by Jeme et al. (Jeme, N. K., (1974) Ann. Immunol. (Paris) 125c:373 and Jeme, N. K., et al., (1982) EMBO 1:234), immunization with an antibody molecule expressing a paratope (antigen-combining site) for a given antigen (e.g., an RF-amide peptide) will produce a group of anti-antibodies, some of which share, with the antigen, a complementary structure to the paratope. Immunization with a subpopulation of the anti-idiotypic antibodies will, in turn, produce a subpopulation of antibodies or immune cell subsets that are reactive to the initial antigen.

The term "fully human antibody" refers to an antibody which comprises human immunoglobulin sequences only. Similarly, "mouse antibody" refers to an antibody which comprises mouse immunoglobulin sequences only and "chicken antibody" refers to an antibody which comprises chicken immunoglobulin sequences only.

"Human/mouse chimeric antibody" refers to an antibody which comprises a mouse variable region ($V_H$ and $V_L$) fused to a human constant region.

"Humanized" anti-RF-amide peptide antibodies are also within the scope of the present invention. Humanized forms of non-human (e.g., murine or chicken) antibodies are chimeric immunoglobulins, which contain minimal sequence derived from non-human immunoglobulin. For the most part, humanized antibodies are human immunoglobulins (recipient antibody) in which residues from a complementary determining region of the recipient are replaced by residues from a complementary determining region of a non-human species (donor antibody), such as mouse, chicken, rat or rabbit, having a desired specificity, affinity and capacity. In some instances, Fv framework residues of the human immunoglobulin are also replaced by corresponding non-human residues.

"Single-chain Fv" or "sFv" antibody fragments include the $V_H$ and/or $V_L$ domains of an antibody, wherein these domains are present in a single polypeptide chain. Generally, the sFv polypeptide further comprises a polypeptide linker between the $V_H$ and $V_L$ domains which enables the sFv to form the desired structure for antigen binding. Techniques described for the production of single chain antibodies (U.S. Pat. Nos. 5,476,786; 5,132,405 and 4,946,778) can be adapted to produce anti-RF-Amide peptide-specific single chain antibodies. For a review of sFv see Pluckthun in *The Pharmacology of Monoclonal Antibodies*, vol. 113, Rosenburg and Moore eds. Springer-Verlag, N.Y., pp. 269-315 (1994).

"Disulfide stabilized Fv fragments" and "dsFv" include molecules having a variable heavy chain ($V_H$) and/or a variable light chain ($V_L$) which are linked by a disulfide bridge.

Antibody fragments within the scope of the present invention also include $F(ab)_2$ fragments which may be produced by enzymatic cleavage of an IgG by, for example, pepsin. Fab fragments may be produced by, for example, reduction of $F(ab)_2$ with dithiothreitol or mercaptoethylamine. A Fab fragment is a $V_L$-$C_L$ chain appended to a $V_H$-$C_{H1}$ chain by a disulfide bridge. A $F(ab)_2$ fragment is two Fab fragments which, in turn, are appended by two disulfide bridges. The Fab portion of an $F(ab)_2$ molecule includes a portion of the Fc region between which the disulfide bridges are located.

An Fv fragment is a $V_L$ or $V_H$ region.

Depending on the amino acid sequences of the constant domain of their heavy chains, immunoglobulins can be assigned to different classes. There are at least five major classes of immunoglobulins: IgA, IgD, IgE, IgG and IgM, and several of these may be further divided into subclasses (isotypes), e.g., IgG-1, IgG-2, IgG-3 and IgG-4; IgA-1 and IgA-2.

The anti-RF-amide peptide antibody molecules of the invention may also be conjugated to a chemical moiety. The chemical moiety may be, inter alia, a polymer, a radionuclide or a cytotoxic factor. Preferably, the chemical moiety is a polymer which increases the half-life of the antibody molecule in the body of a subject. Suitable polymers include, but are by no means limited to, polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Methods for producing PEGylated anti-IL8 antibodies which are described in U.S. Pat. No. 6,133,426, which is herein incorporated by reference, can be applied to the production of PEGylated anti-RF-Amide peptide antibodies of the invention. Lee, et al., (1999) (Bioconj. Chem. 10:973-981) discloses PEG conjugated single-chain antibodies. Wen, et al., (2001) (Bioconj. Chem. 12:545-553) discloses conjugating antibodies with PEG which is attached to a radiometal chelator (diethylenetriaminpentaacetic acid (DTPA)).

The antibody molecules of the invention may also be conjugated with radioisotopic labels such as $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{51}$Cr, $^{57}$To, $^{226}$Ra, $^{60}$Co, $^{59}$Fe, $^{57}$Se, $^{152}$Eu, $^{67}$CU, $^{217}$Ci, $^{211}$At, $^{212}$Pb, $^{47}$Sc, $^{109}$Pd, $^{234}$Th, and $^{40}$K, and non-radioisotopic labels such as $^{157}$Gd, $^{55}$Mn, $^{52}$Tr, $^{56}$Fe.

The antibodies of the invention may also be conjugated with fluorescent or chemilluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibody molecules may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *momordica charantia* inhibitor, curcin, crotin, *saponaria officinalis* inhibitor, mitogellin, restrictocin, phenomycin, and enomycin.

Any method known in the art for conjugating the antibody molecules of the invention to the various moieties may be employed, including those methods described by Hunter, et al., (1962) Nature 144:945; David, et al., (1974) Biochemistry 13:1014; Pain, et al., (1981) J. Immunol. Meth. 40:219; and Nygren, J., (1982) Histochem. and Cytochem. 30:407.

Methods for conjugating antibodies are conventional and very well known in the art.

Pharmaceutical Compositions

RF-amide peptides and antibody molecules of the invention can be administered, preferably for therapeutic purposes, to a subject, preferably in a pharmaceutical composition. Preferably, a pharmaceutical composition includes a pharmaceutically acceptable carrier. The RF-Amide peptides and antibody molecules may be used therapeutically (e.g., in a pharmaceutical composition) to stimulate or block the activity of the SP9155 receptor and, thereby, to treat any medical condition caused or mediated by the receptor. Blocking the binding of the RF-amide peptides of the invention to the SP9155 receptor may block the effect that said peptides have on the activity of the receptor. As discussed above, the SP9155 receptor has been connected to metabolic disorders such as obesity and to mechanisms such as pain and analgesia.

Pharmaceutically acceptable carriers are conventional and very well known in the art. Examples include aqueous and nonaqueous carriers, stabilizers, antioxidants, solvents, dispersion media, coatings, antimicrobial agents, buffers, serum proteins, isotonic and absorption delaying agents, and the like that are physiologically compatible. Preferably, the carrier is suitable for injection into a subject's body. Generally, compositions useful for parenteral administration of such drugs are well known; e.g., *Remington's Pharmaceutical Science,* 17th Ed. (Mack Publishing Company, Easton, Pa., 1990).

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions and by the use of surfactants.

The pharmaceutical compositions of the invention may be administered in conjunction with a second pharmaceutical composition or substance. In preferred embodiments, the second composition is an anti-obesity drug or an analgesic. When a combination therapy is used, both compositions may be formulated into a single composition for simultaneous delivery or formulated separately into two or more compositions (e.g., a kit).

Anti-obesity drugs may include sibutramine, phentermine or orlistant.

Analgesics may include aspirin, acetominophen, codein, morphine, aponorphine, normorphine, etorphine, buprenorphine, hydrocodone, racemorphan, levorphanol, butorphand, methadone, demerol, ibuprofen or oxycodone.

Pharmaceutical compositions of the invention may also include other types of substances, including small organic molecules and inhibitory ligand analogs, which can be identified using the assays described herein.

The formulations may conveniently be presented in unit dosage form and may be prepared by any methods well known in the art of pharmacy. See, e.g., Gilman et al. (eds.) (1990), *The Pharmacological Bases of Therapeutics,* 8th Ed., Pergamon Press; and *Remington's Pharmaceutical Sciences,* supra, Easton, Penn.; Avis et al. (eds.) (1993) *Pharmaceutical Dosage Forms: Parenteral Medications* Dekker, N. Y. ; Lieberman et al. (eds.) (1990) *Pharmaceutical Dosage Forms*: Tablets Dekker, N. Y.; and Lieberman et al. (eds.) (1990), *Pharmaceutical Dosage Forms: Disperse Systems* Dekker, N. Y.

The dosage regimen involved in a therapeutic application may be determined by a physician, considering various factors which may modify the action of the therapeutic substance, e.g., the condition, body weight, sex and diet of the patient, the severity of any infection, time of administration, and other clinical factors.

Often, treatment dosages are titrated upward from a low level to optimize safety and efficacy. Dosages may be adjusted to account for the smaller molecular sizes and possibly decreased half-lives (clearance times) following administration.

An "effective amount" of a composition of the invention may be an amount that will ameliorate one or more of the well-known parameters that characterize medical conditions caused or mediated by the SP9155 receptor or a functional fragment thereof.

Typical protocols for the therapeutic administration of such substances are well known in the art. Pharmaceutical compositions of the invention may be administered, for example, by parenteral routes (e.g., intravenous injection, intramuscular injection, subcutaneous injection, intratumoral injection or by infusion) or by a non-parenteral route (e.g., oral administration, pulmonary administration or topical administration).

Compositions can be administered with medical devices known in the art. For example, in a preferred embodiment, a pharmaceutical composition of the invention can be administered by injection with a hypodermic needle.

The pharmaceutical compositions of the invention may also be administered with a needleless hypodermic injection device; such as the devices disclosed in U.S. Pat. Nos. 5,399,163; 5,383,851; 5,312,335; 5,064,413; 4,941,880; 4,790,824 or 4,596,556.

Examples of well-known implants and modules useful in the present invention include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments.

Anti-Sense Molecules

The present invention also encompasses anti-sense oligonucleotides capable of specifically hybridizing to nucleic acids (e.g., genomic DNA or mRNA) encoding an RF-Amide peptide of the invention, preferably having an amino acid sequence defined by any of SEQ ID NOs: 4-11 or 13-18 or a subsequence thereof so as to prevent expression of the nucleic acid.

This invention further provides pharmaceutical compositions comprising (a) an amount of an oligonucleotide effective to modulate the activity of the SP9155 receptor by passing through a cell membrane and binding specifically with mRNA encoding an RF-Amide peptide of the invention in the cell so as to prevent its translation and (b) a pharmaceutically acceptable carrier capable of passing through a cell membrane. In an embodiment, the oligonucleotide is coupled to a substance that inactivates mRNA (e.g., a ribozyme).

EXAMPLES

The following Examples are intended for exemplification of the present invention only and should not be construed to limit the scope of the invention in any way.

Abbreviations

*GenScan*: a gene prediction algorithm (Burge, et al., (1997) J. Mol. Biol. 268 (1):78-94).

*Human virtual transcripts database (VTS)*: Running GenScan, genes or exons were predicted from human genomic DNA which is available in public databases. VTS is a collection of all those predicted human genes or exons. Both a DNA and protein version of VTS were generated.

Example 1

Identification the Human RF-Amide Peptide Precursor Protein

RF-amide peptides are members of a well known neuropeptide family and are derived from a propeptide with a carboxy-terminal "RFG(K/R)" motif. In general, "G(K/R)" is a proteinase digestion and amidation signal. Proteolytic digestion and amidation are steps which occur when the propeptide is processed into a mature peptide with an RF-amide carboxy-terminus.

Since most RF-amide peptide precursors contain more than one RFG(K/R) motif, the VTS protein database was searched for peptides bearing one or more RFGR motifs. We identified VTS164407 which was found to contain an exon with two RFG(K/R) motifs. Further analysis revealed that this exon contained a start codon at the beginning and a stop codon at the end. Analysis of the exon with PSORT (a free software for protein subcellular localization prediction; Nakai, et al., (1999) Trends Biochem. Sci. 24(1):34-36), predicted that this exon has a leader peptide and no transmembrane domain, which suggested that the exon encoded a secreted protein. This exon may be referred to as the "RF-Amide peptide precursor".

Since, in general, RF-amide peptide precursors are also secreted, the cDNA which encodes the gene was isolated. A one nucleotide difference between the genomic exon and the cDNA clone was identified. This difference could represent a polymorphism. The nucleotide sequence and the corresponding, deduced amino acid sequence is set forth in SEQ ID NOs: 3 and 4, respectively.

Example 2

Identification of the Mouse Homologue of the Human RF-Amide Peptide Precursor Gene.

The mouse homologue of the Human RF-Amide peptide precursor gene was identified by BLAST searching a public, expressed sequence tag (EST) database using the Human RF-Amide peptide precursor gene as a query. In this search, Mouse EST BF167714 was identified to be homologous to human RF-Amide peptide precursor. In addition, a public Mouse genomic DNA database was searched using the Human RF-Amide peptide precursor gene as a query. Again, a Mouse homologue was identified in the second search which was determined, by sequence alignment, to be identical to the Mouse homologue which was identified in the first search. The full-length Mouse RF-Amide peptide precursor gene was deduced from the clones which were identified.

Based on the deduced Mouse RF-Amide peptide precursor DNA sequence, the cDNA of the Mouse RF-Amide peptide precursor was cloned. The nucleotide sequence and the corresponding, deduced amino acid sequence is set forth in SEQ ID NOs: 12 and 13, respectively.

Example 3

Possible Functional Peptides Derived from both Human and Mouse RF-Amide Peptide Precursor Genes.

We deduced the following, possible, functional RF-amide peptides based upon the assumption that RFG(K/R) would be at the carboxy-terminus.

The peptides derived from human RF-Amide peptide precursor are as follows:

```
The peptides derived from human RF-Amide
peptide precursor are as follows:
Human P51:
EHAGCRFRF-amide                            (SEQ ID NO:5)

Human P242:
GLQTSGREHAGCRFRF-amide                     (SEQ ID NO:6)

Human P552:
ASQPQALLVIARGLQTSGREHAGCRFRF-amide         (SEQ ID NO:7)

Human P52:
GGFSFRF-amide                              (SEQ ID NO:8)

Human P513:
KGGFSFRF-amide                             (SEQ ID NO:9)

Human P517:
KKGGFSFRF-amide                            (SEQ ID NO:10)

Human P518:
```

```
                                    -continued
TSGPLGNLAEELNGYSRKIKGGFSFRF-amide        (SEQ ID NO:11)

The peptides derived from mouse RF-Amide peptide
precursor are as follows:
Mouse P51:
EHTGFRL-amide                            (SEQ ID NO:14)

Mouse P52:
GGFSFRF-amide                            (SEQ ID NO:15)

Mouse P513:
KGGFSFRF-amide                           (SEQ ID NO:16)

Mouse P517:
RKGGFSFRF-amide                          (SEQ ID NO:17)

Mouse P518:
ASGPLGTLAEELSSYSRRKGGFSFRF-amide         (SEQ ID NO:18)
```

Example 4

Assays a. Intracellular $Ca^{2+}$ Concentration Measurement.

In the following example, Fluorometric Imaging Plate Reader (FLIPR) Assays were used to determine that Human P518, P517, P52, P513 and P51 are ligands for the Human SP9155 receptor. As discussed below, the assay may be adapted for determining whether a sample is an agonist or an antagonist to the receptor.

HEK293 cells, grown in DMEM containing 10% FCS until 80-90% confluence, were transfected with either an expression vector carrying SP9155 receptor cDNA or an expression vector lacking SP9155 receptor DNA using SuperFect transfection agent. The next day, cells were trypsinized off culture plates and washed with PBS lacking $Ca^{2+}/Mg^{2+}$. The cells were then seeded at a density of 35,000 cells per 100 µl medium into 96-well plates that were pre-coated with poly-D-lysine (Becton Dickinson). On the third day following transfection, medium was removed from cells and 100 µl Hank's balanced salt solution (lacking phenol red) containing 4 µM of Fluo-3, AM (Molecular Probes), 20 mM Hepes, pH 7.4, 0.1% (w/v) BSA and 250 mM probenecid added and subsequently incubated at 37° C., 5% $CO_2$ for 1 hour. The cells were then washed three times with 150 µl wash buffer containing HANK's BSS, 40 mM Hepes, pH 7.4 and 250 mM probenecid. One hundred µl of the wash buffer was added after the final wash and $Ca^{2+}$flux was measured after addition of 40 µl of wash buffer containing each respective peptide. The FLIPR instrument (Molecular Device) was used in the measurement of $Ca^{2+}$flux.

Data which was generated in these assays is shown below in Table 3:

TABLE 3

Peptide Potency

| Ligand[1] | | $EC_{50}$ (nM)[2] |
|---|---|---|
| Human P518 | (SEQ ID NO:11) | 7.0 ± 3.0 |
| Human P517 | (SEQ ID NO:10) | 235 ± 6 |
| Human P52 | (SEQ ID NO:8) | 245 ± 58 |
| Human P513 | (SEQ ID NO:9) | 258 ± 20 |
| Human P51 | (SEQ ID NO:5) | 1560 ± 170 |

[1] Each peptide tested was carboxy-terminally amidated.
[2] The values represent mean ± standard deviation; n = 5.

The FLIPR assay may also be used to screen samples for agonist or antagonist activity. In these assays, the test cells may be simultaneously contacted with a peptide ligand (or with any other SP9155 receptor ligand) and the sample. A negative control experiment may include contacting the test cells with the ligand and a blank (e.g., water or any other substance which is known to not be an agonist or antagonist). A positive control experiment may include contacting the test cells with the ligand and a substance which is known to agonize or antagonize SP9155 receptor/ligand binding.

A sample may be identified as containing an antagonist upon its ability to decrease the extent of $Ca^{2+}$ mobilization caused by ligand/receptor binding (i.e., to decrease the FLIPR signal) as compared to that of the same experiment performed without the sample. Conversely, a sample may be identified as containing an agonist upon its ability to increase the extent of $Ca^{2+}$ mobilization caused by ligand/receptor binding (i.e., to increase the FLIPR signal) as compared to that of the same experiment preformed without the sample.

b. Radioligand Binding Assay.

In this example, Radioligand Binding Assays are used to determine that Human P518 is a ligand for the Human SP9155 receptor. As discussed below, the assay may be adapted for determining whether a sample is an agonist or an antagonist.

Radioligand binding assays are performed to test the ability of the SP9155 receptor, when expressed in cultured cells, to bind $^3$H-labeled P518. The ORF of SP9155 is cloned in the expression vector pCR3.1 (pCR3.1-SP9155). COS-7 cells are transfected with pCR3.1-SP9155 or pCR3.1 alone (mock transfection). Two days after transfection, the normal growth medium DMEM/10% FCS is replaced by either Opti-MEM or DMEM-Opti-MEM/5% FCS. The cells are allowed to grow one more day and then membranes are prepared for use in the binding assay. Unlabeled P518 at 1 µM is used to determine non-specific binding. After a total of three days from transfection, membranes are prepared from the transfectant cells and specific binding to $^3$H-P518 is observed.

For saturation binding, 150 µl binding assay buffer (30 mM Hepes, pH 7.4, 10 mM $CaCl_2$, 10 mM $MgCl_2$, 0.05% fatty acid-free BSA (w/v), kept cold on ice) containing 24 µg of membranes are mixed with 50 µl of binding assay buffer containing 2% (v/v) DMSO cold P518 (1 µM). $^3$H-P518/ ethanol is added to the assays at increasing concentrations. The reactions are incubated for 1 hour at 4° C. while rotating slowly. Multiscreen FB filters (Millipore) pre-soaked with 50 µl binding assay buffer for 1 hour at room temperature are used to filter the binding assays and the filters are washed twice with 100 µl 50 mM Tris-Cl, pH 7.5 (ice cold). Fifty microliters of scintillation fluid is added to the filters and counted to detect the bound radioligands.

For radioligand competition assays, 160 µl binding assay buffer containing appropriate membranes are mixed with 20 µl of binding assay buffer containing 6% DMSO (v/v) and various concentrations of candidate competing compounds. A final 20 µl of binding assay buffer containing 6% (v/v) DMSO and 1 µl of $^3$H-P518/ethanol (NEN, 50 nM) is added to start the binding reaction. The final concentration of radioligand is 0.25 nM. Incubation conditions are the same as that used for the above described saturation assays. A sample may be identified as containing an agonist or antagonist upon its ability to decrease binding of the ligand to the receptor as compared to that of the same experiment performed without the sample.

A negative control experiment may include contacting the membranes with the ligand and a blank (e.g., water or any other substance which is known to not be an agonist or antagonist). A positive control experiment may include contacting the test cells with the ligand and a substance which is known to agonize or antagonize SP9155 receptor/ligand binding.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application, the disclosures of which are incorporated herein by reference in their entireties for all purposes.

We claim:

1. A method for identifying an agonist or antagonist of an SP9155 receptor comprising:
    (a) contacting a cell expressing human SP9155 receptor or a ligand-binding fragment thereof which receptor or fragment thereof is capable of binding one or more polypeptide ligands comprising an amino acid sequence selected from the group consisting of SEQ ID NOs: 4-11 and 13-18, wherein the carboxy-terminus of each of said polypeptide ligands are amidated, in the presence of a known amount of polypeptide ligand for the human SP9155 receptor or ligand-binding fragment thereof, wherein said polypeptide ligand comprises an amino acid sequence selected from the group consisting of SEQ ID NOs: 4-11 and 13-18, wherein the carboxy-terminus of said polypeptide ligand is amidated, with a sample to be tested for the presence of said agonist or antagonist; and
    (b) measuring calcium mobilization by the cell;
    whereby the sample is identified as containing an antagonist by measuring substantially reduced calcium mobilization compared to what would be measured in the absence of the sample and whereby the sample is identified as containing an agonist by measuring substantially increased calcium mobilization compared to what would be measured in the absence of the sample.

2. The method of claim 1 wherein the polypeptide ligand is a polypeptide comprising an amino acid sequence selected from SEQ ID NOs: 5-11 and 14-18 wherein the carboxy-terminus of said polypeptide ligand is amidated.

3. The method of claim 1 wherein the receptor comprises the amino acid sequence of SEQ ID NO: 2.

4. The method of claim 1 wherein the calcium mobilization is measured by contacting the calcium with a calcium indicator and then measuring fluorescence of said indicator.

5. The method of claim 4 wherein the calcium indicator is 1-[2-Amino-5-(2,7-dichloro-6-hydroxy-3-oxy-9-xanthenyl)phenoxy)phenoxy]-2-(2'-amino-5'-methylphenoxy) ethane-N,N,N',N'-tetraacetic acid, pentaacetoxymethyl ester.

6. The method of claim 3 wherein said cell is a HEK293 cell.

7. The method of claim 2 wherein said polypeptide ligand is a polypeptide comprising an amino acid sequence selected from the group consisting of SEQ ID NOs: 5, 8, 9, 10 and 11, wherein the carboxy-terminus of said polypeptide ligand is amidated.

8. The method of claim 7 wherein the polypeptide ligand is a polypeptide comprising the amino acid sequence set forth in SEQ ID NO: 11, wherein the carboxy-terminus of said polypeptide ligand is amidated.

9. The method of claim 8 wherein the polypetide ligand is a polypeptide which consists of the amino acid sequence set forth in SEQ ID NO: 11, wherein the carboxy-terminus of said polypeptide ligand is amidated.

10. The method of claim 8 wherein the receptor comprises the amino acid sequence of SEQ ID NO: 2.

11. The method of claim 9 wherein the receptor comprises the amino acid sequence of SEQ ID NO: 2.

12. The method of claim 10 wherein the calcium mobilization is measured by contacting the calcium with 1-[2-Amino-5-(2,7-dichloro-6-hydroxy-3-oxy-9-xanthenyl)phenoxy]-2-(2'-amino-5'-methylphenoxy) ethane-N,N,N',N'-tetraacetic acid, pentaacetoxymethyl ester and then measuring fluorescence of said indicator.

13. The method of claim 11 wherein the calcium mobilization is measured by contacting the calcium with 1-[2-Amino-5-(2,7-dichloro-6-hydroxy-3-oxy-9-xanthenyl)phenoxy]-2-(2'-amino-5'-methylphenoxy) ethane-N,N,N',N'-tetraacetic acid, pentaacetoxymethyl ester and then measuring fluorescence of said indicator.

14. The method of claim 2 wherein the receptor comprises the amino acid sequence of SEQ ID NO: 2 or a ligand-binding fragment thereof.

15. The method of claim 2 wherein the polypeptide ligand is a polypeptide consisting of an amino acid sequence selected from the group consisting of SEQ ID NOs: 5-11 and 14-18 wherein the carboxy-terminus of said polypeptide ligand is amidated.

16. The method of claim 15 wherein the receptor consists of the amino acid sequence set forth in SEQ ID NO: 2.

17. The method of claim 7 wherein the receptor consists of the amino acid sequence set forth in SEQ ID NO: 2.

18. The method of claim 2 wherein said cell is expressing the human SP9155 receptor.

19. The method of claim 7 wherein the polypeptide ligand comprises the amino acid sequence set forth in SEQ ID NO: 5.

20. The method of claim 7 wherein the polypeptide ligand consists of the amino acid sequence set forth in SEQ ID NO: 5.

21. The method of claim 7 wherein the polypeptide ligand comprises the amino acid sequence set forth in SEQ ID NO: 8.

22. The method of claim 7 wherein the polypeptide ligand consists of the amino acid sequence set forth in SEQ ID NO: 8.

23. The method of claim 7 wherein the polypeptide ligand comprises the amino acid sequence set forth in SEQ ID NO: 9.

24. The method of claim 7 wherein the polypeptide ligand consists of the amino acid sequence set forth in SEQ ID NO: 9.

25. The method of claim 7 wherein the polypeptide ligand comprises the amino acid sequence set forth in SEQ ID NO: 10.

26. The method of claim 7 wherein the polypeptide ligand consists of the amino acid sequence set forth in SEQ ID NO: 10.

27. The method of claim 7 wherein the receptor comprises the amino acid sequence set forth in SEQ ID NO: 2.

* * * * *